(12) United States Patent
Welz et al.

(10) Patent No.: US 8,232,245 B2
(45) Date of Patent: Jul. 31, 2012

(54) CASPOFUNGIN FORMULATIONS

(75) Inventors: Christian Welz, Brixlegg (AT);
Gottfried Stubauer, Innsbruck (AT);
Andreas Schmarda, Goetzens (AT);
Herwig Jennewein, Absam (AT); Ingolf Macher, Woergl (AT); Johannes Ludescher, Breitenbach (AT)

(73) Assignee: Sandoz AG, Basel (CH)

( * ) Notice: Subject to any disclaimer, the term of this patent is extended or adjusted under 35 U.S.C. 154(b) by 508 days.

(21) Appl. No.: 12/374,489

(22) PCT Filed: Jul. 24, 2007

(86) PCT No.: PCT/EP2007/057623
§ 371 (c)(1),
(2), (4) Date: Jan. 21, 2009

(87) PCT Pub. No.: WO2008/012310
PCT Pub. Date: Jan. 31, 2008

(65) Prior Publication Data
US 2009/0170753 A1 Jul. 2, 2009

(30) Foreign Application Priority Data

Jul. 26, 2006 (EP) .................................... 06117886
Jun. 6, 2007 (EP) .................................... 07109723

(51) Int. Cl.
*A61K 38/12* (2006.01)
(52) U.S. Cl. ...................... 514/3.6; 514/3.4; 514/21.1
(58) Field of Classification Search .................. None
See application file for complete search history.

(56) References Cited

U.S. PATENT DOCUMENTS

| | | | |
|---|---|---|---|
| 5,378,804 A | | 1/1995 | Balkovec |
| 5,952,300 A | | 9/1999 | Nerurkar |
| 5,997,856 A | * | 12/1999 | Hora et al. ............ 424/85.2 |
| 6,780,881 B2 | | 8/2004 | Linder |
| 6,900,184 B2 | | 5/2005 | Cohen |
| 7,351,723 B2 | | 4/2008 | Linder |
| 2007/0231308 A1 | * | 10/2007 | Larsen et al. ............ 424/93.21 |

FOREIGN PATENT DOCUMENTS

| | | |
|---|---|---|
| CN | 1222082 A | 10/1997 |
| EP | 0620232 | 10/1994 |
| EP | 1 339 430 | 3/2003 |
| EP | 0 904 098 | 6/2003 |
| EP | 0904098 B1 | 6/2003 |
| EP | 1 785 432 | 5/2007 |
| WO | 94/21677 | 9/1994 |
| WO | 96/24613 | 8/1996 |
| WO | 97/39763 A1 | 10/1997 |
| WO | 97/47645 | 12/1997 |
| WO | 02/41919 | 5/2002 |
| WO | 2007/057141 | 5/2007 |

OTHER PUBLICATIONS

U.S. Appl. No. 10/583,159, filed Jun. 16, 2006.*
U.S. Appl. No. 11/766,132, filed Jun. 21, 2007.*
U.S. Appl. No. 12/093,657, filed May 14, 2008.*
U.S. Appl. No. 12/303,438, filed Dec. 4, 2008.*
U.S. Appl. No. 12/303,411, filed Dec. 4, 2008.*
Merck Index online, edition 2001-2005 by Merck & Co., Inc. Whitehouse Station, NJ, USAI.
Berge S.M., Bighley L.D., Monkhouse D.C.: "Pharmaceutical Salts", Journal of Pharmaceutical Sciences, 66 (1),1977, pp. 1-19.
Strickley R.G.: "Parenteral Formulations of Small Molecules Therapeutics Marketed in the United States (1999)—Part I"; PDA Journal of Pharmaceutical Science & Technology, 53 (6), 1999, 324-349.
Powell M.F. et al.: Compendium of excipients for parenteral formulations, PDA Journal of Pharmaceutical Science and Technology, 52 (5), 1998, pp. 238-311.
ICH guidelines (International Conference on Harmonization of Technical Requirements for Registration of Pharmaceuticals for Human Use, ICH Harmonized Tripartite Guideline, Impurities: Guideline for Residual Solvents, Q3C(R3), Current Step 4 version, Parent Guideline dated Jul. 17, 1997).
Merck Index, 13th edition, monograph No. 1899.
Beltz K et al., Klinische Pädiatrie (2006) vol. 218, No. 3, pp. 177-179—abstract ex Database Medline, XP002442942.
Cancidas Product Monograph, Jan. 26, 2006, by Merck Frosst Canada, Ltd.
Moiseeva E.V. et al., Pharmaceutical Chemistry Journal, vol. 36, No. 12, 2002, pp. 669-674.
Borchert S.J. et al., Journal of Parenteral Science & Technology, vol. 40, No. 5, 1986, pp. 212-241.
Thomas W.H., et al, New Zealand Medical Journal, Aug. 28, 1974, pp. 170-178.
International Search Report and Written Opinion issued in PCT/EP2007/057623.
Chinese Office Action dated Jun. 24, 2011 (for Chinese equivalent application) and its English Translation.
Groves, Particulate Matter in Parenteral Products, Encyclopedia of Pharmaceutical Technology, vol. 11, Eds.: J. Swarbrick & J.C. Boylan, Marcel Kekker, Inc., US, 1995.
Powell, Compendium of Excipients for Parenteral Formulations, Pharmaceutical Research and Development, Genentech, Inc., South San Francisco, California, Review Article, PDA Journal of Pharmaceutical Science & Technology, Feb. 16, 1998, pp. 238-311.
The United States Pharmacopeia Convention, Meeting at Washington D.C. Apr. 12-16, 2000, Prepared by the Council of Experts and published by the Board of Trustees, Particulate Matter in Injections (Physical Tests), pp. 2338-2344.

* cited by examiner

*Primary Examiner* — Jeffrey E Russel
(74) *Attorney, Agent, or Firm* — Jeffrey S. Melcher; Manelli Selter PLLC

(57) ABSTRACT

The present invention relates to pharmaceutical compositions comprising a pharmaceutically acceptable salt of caspofungin as active ingredient being useful for the prevention and/or treatment of fungal infections. The compositions additionally comprise specific bulking agents and small amounts or no amounts of an additional pH modifier and may be in a liquid or solid form, e.g. may be lyophilized compositions. The compositions show good stability and reduced amounts of sub-visible particulate matter formed in solutions which are reconstituted from the lyophilized product.

25 Claims, 6 Drawing Sheets

Figure 1: Total Impurities

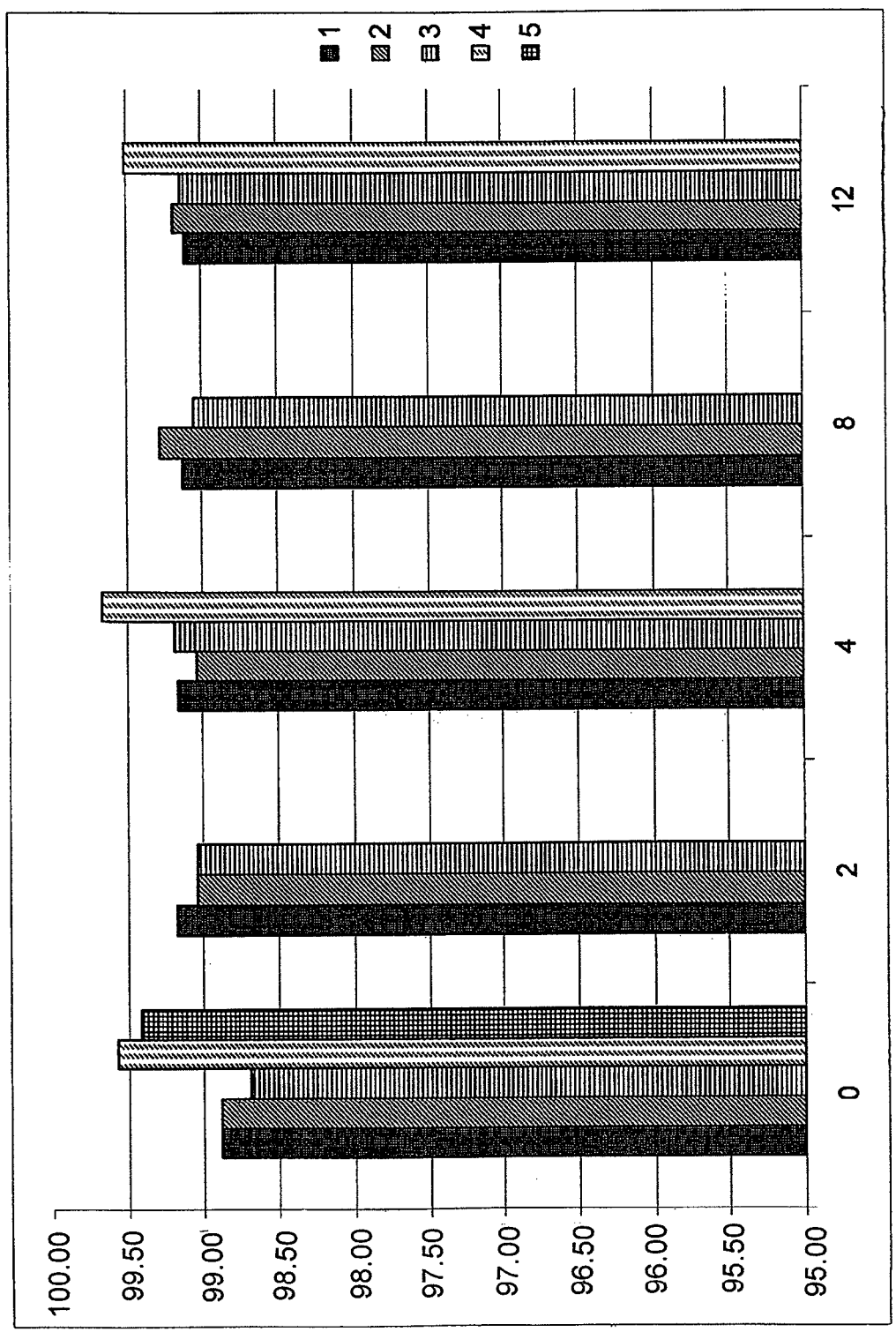
Figure 2: Assay for Caspofungin

Figure 3: Sub-visible Particles > 10 µm

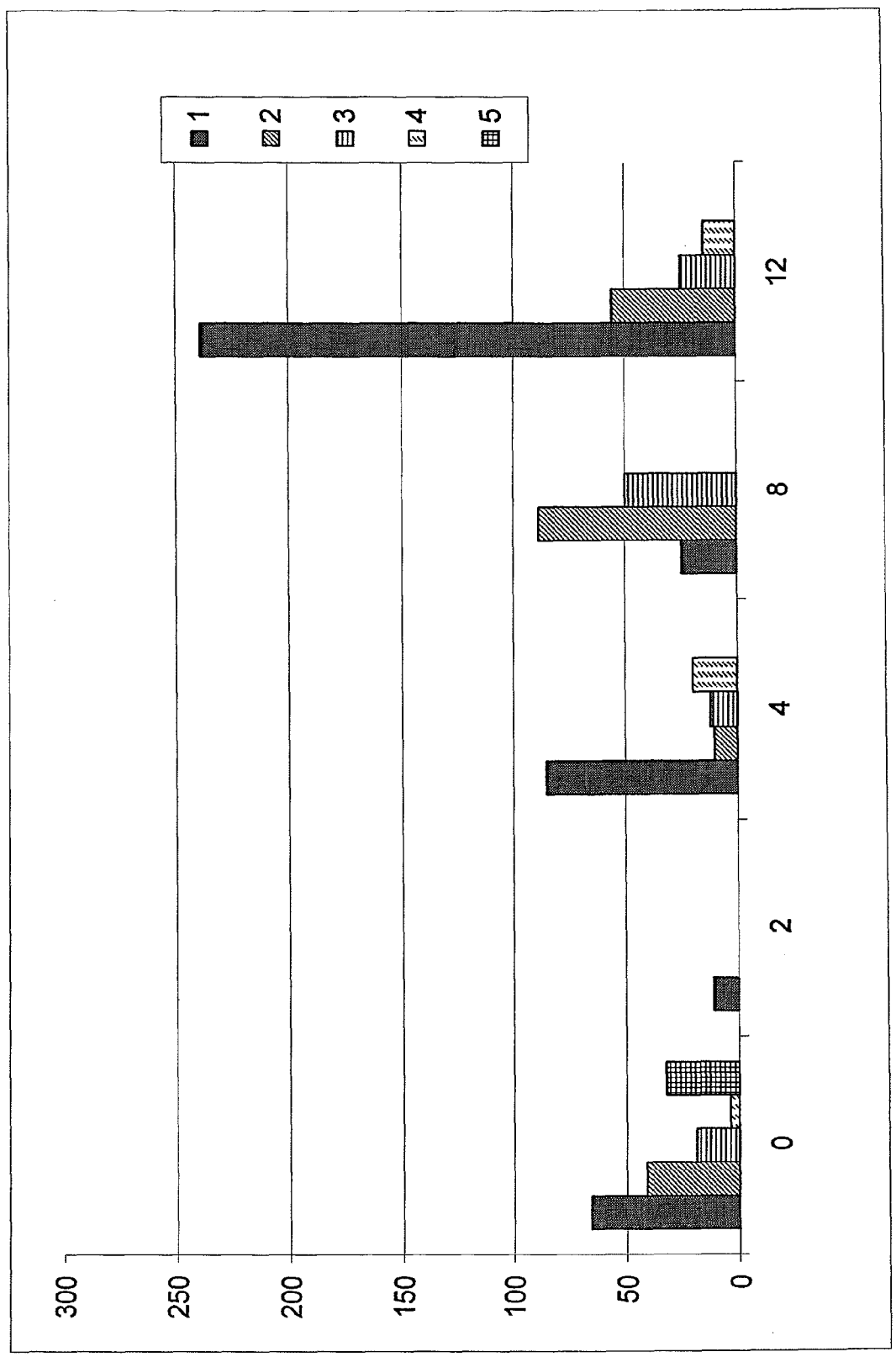
Figure 4: Sub-visible Particles > 25 μm

Figure 5: X-Ray Powder Diffraction (XRPD) Pattern of Crystalline Caspofungin Propionate
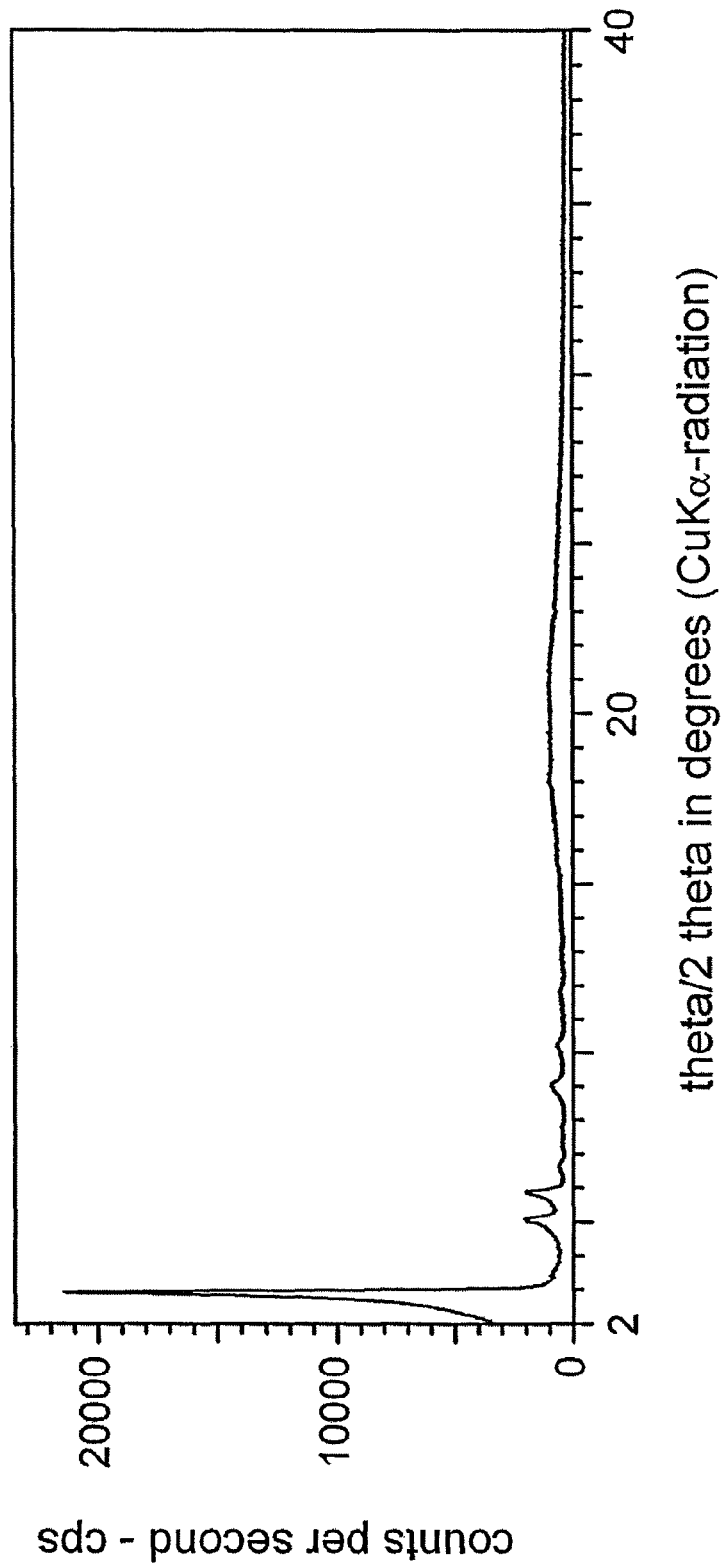

Figure 6: X-Ray Powder Diffraction (XRPD) Pattern of Amorphous Caspofungin Propionate
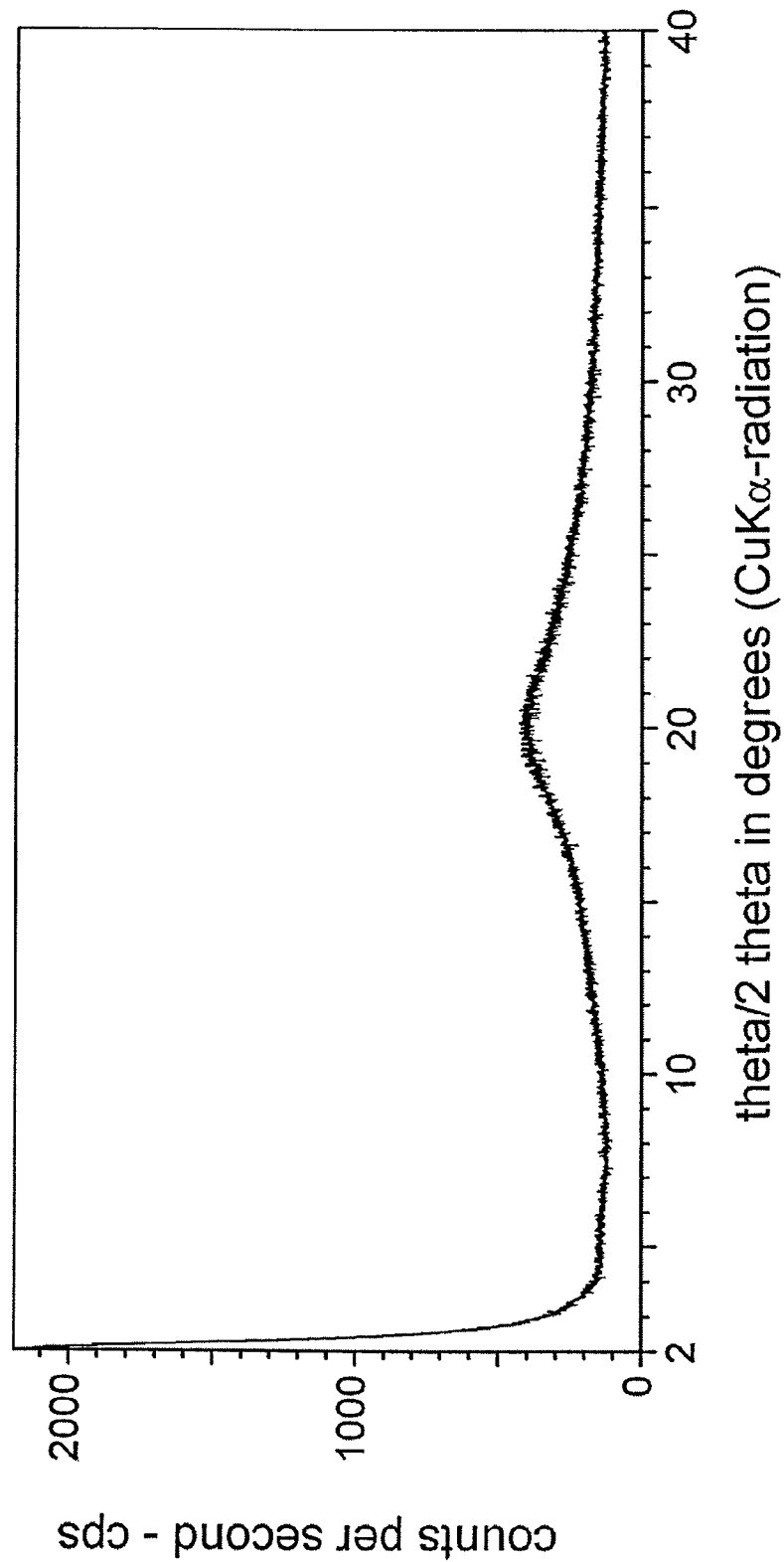

CASPOFUNGIN FORMULATIONS

CROSS-REFERENCE TO RELATED APPLICATIONS

This application is a national stage entry under 35 U.S.C. 371 of International Application No. PCT/EP2007/057623, filed 24 Jul. 2007, designating the United States. This application claims foreign priority under 35 U.S.C. 119 and 365 to European Patent Application Nos. 06117886.9, filed 26 Jul. 2006, and 07109723.2, filed 6 Jun. 2007.

FIELD OF THE INVENTION

The present invention relates to pharmaceutical compositions comprising a pharmaceutically active ingredient which is useful for the prevention and/or treatment of fungal infections and/or conditions arising from said infections. More particularly the invention relates to compositions comprising the compound caspofungin as active ingredient, specific bulking agents and small amounts or no amounts of an additional pH modifier which compositions are liquid or solid compositions, e.g. lyophilized compositions.

BACKGROUND OF THE INVENTION

The compositions of the present invention contain as pharmaceutically active ingredient caspofungin free base being a compound of formula I

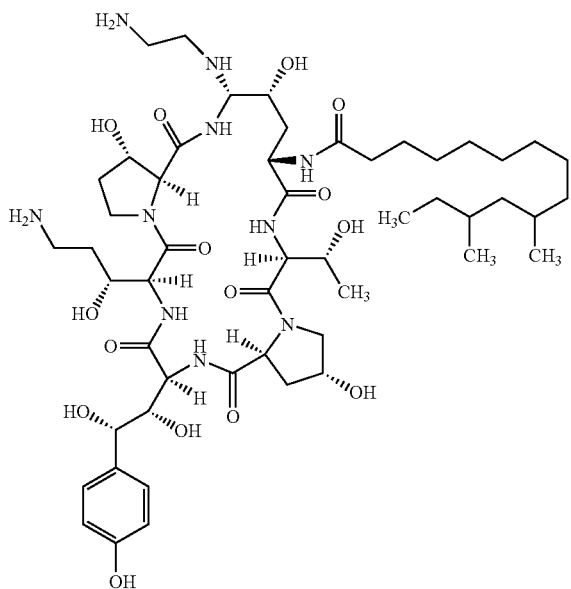

which is known to be an effective antifungal and anti-protozoal agent. The aza cyclohexapeptide compound caspofungin belonging to the echinocandin family has the CAS Registry Number 162808-62-0 and the CAS Name 1-[(4R,5S)-5-[(2-Aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$ (Merck Index online, edition 2001-2005 by Merck & Co., Inc., Whitehouse Station, N.J., USA). Caspofungin exists in a variety of pharmaceutically acceptable salts such as caspofungin diacetate as described e.g. in European Patent EP 0 904 098 B1. Caspofungin and methods for preparing it have been described e.g. in WO 94/21677 and EP 620232 which disclose inter alia caspofungin as being particularly useful in the control of mycotic infections among many other aza cyclohexapeptide compounds and their pharmaceutically acceptable salts such as hydrochloric, sulfuric, citric or other acid addition salts. Caspofungin (tris)-trifluoroacetate salt and its (tris)-hydrochloride salt have been described. WO96/24613 discloses additional processes to prepare caspofungin and in particular caspofungin diacetate salt. Caspofungin is effective in the prevention and/or treatment of infections caused by filamentous fungi and yeasts such as *Aspergillus* sp., *Histoplasma* sp., *Coccidioides* sp., *Blastomyces* sp. and/or *Candida* sp., as well as in preventing and/or controlling and/or treating infections such as pneumonia caused by *Pneumocystis jiroveci* (previously classified as *Pneumocystis carinii*). Caspofungin may be administered parenterally, e.g. intravenously by use of compositions being either lyophilized or liquid formulations.

European Patent EP 0 904 098 B1 or U.S. Pat. No. 5,952,300 discloses lyophilized formulations comprising caspofungin, 25 mM to 50 mM additional acetate buffer, and bulking agents such as sucrose and/or mannitol or mixtures thereof. Said formulations are stated to have enhanced chemical stability due to the use of an acetate buffer instead of a tartrate buffer. The switch to the acetate buffer is reported to result in fewer degradation products and in a more stable lyophilized formulation having an extended shelf life. The preparation of the liquid formulation which is to be lyophilized to give the final product for parenteral, in particular intravenous administration, is, however, a time consuming and fastidious procedure necessitating 2 steps of a pH-adjustment.

It has furthermore been reported that reconstitution of such lyophilized pharmaceutical compositions with a carrier solution, such as e.g. water for injection, or physiological saline, or aqueous solution of 5% glucose may lead to the formation of visible and/or sub-visible particles in the solution, as described e.g. in WO 02/41919 A1 related to pantoprazole injectable formulations. Injectable solutions such as solutions reconstituted from sterile e.g. lyophilized solids should normally be essentially free from particles that can be observed on visual inspection. For patient safety, it is also desirable that such injectable solutions have a low number of sub-visible particles. Such particles may be extraneous particles being derived e.g. from the glass of the vial containing the lyophilized product. Such sub-visible particles may e.g. result in an increased risk of embolia in a patient receiving the reconstituted product intravenously. It is known that ethylenediamine tetraacetic acid (EDTA) or its sodium salt are generally used to reduce the formation of particles in conventional pharmaceutical formulations intended for parenteral administration, e.g. lyophilized solids to be reconstituted or ready-to-use liquid formulations, such as described e.g. in WO 02/41919 A1 for pantoprazole formulations, and in U.S. Pat. No. 6,900,184 B2 for compositions containing piperacillin and tazobactam.

It would be desirable to provide a liquid or lyophilized composition comprising caspofungin which has a reduced number of sub-visible particles to increase safety for patients even without any addition of EDTA or related substances. It is furthermore desirable that such compositions have a good stability and a long shelf-life and may be manufactured by a simple and fast method.

Furthermore, an additional salt of caspofungin would be desirable to offer to the skilled person the possibility to use an alternative salt form of caspofungin. Said novel salt should be stable, should allow large scale preparation and should be easy for handling when preparing a pharmaceutical composition comprising the caspofungin salt.

SUMMARY OF THE INVENTION

The inventors have now surprisingly found that pharmaceutical compositions comprising a pharmaceutically acceptable salt of caspofungin and pharmaceutically acceptable excipients such as bulking agents suitable to form a lyophilized cake, are surprisingly stable in the presence of only low amounts of pH-modifiers and even in the substantial absence of any additional pH-modifier or buffer, e.g. without any additional acetate buffer or any other substance known to be a buffering agent and/or having buffering capacity.

The inventors have found that the addition of only a small amount of a pH modifier such as the addition of acetic acid in an amount below 0.3 mole equivalents of said caspofungin salt is sufficient to obtain a stable formulation. The inventors have further found that the addition of a pH modifier is not even necessary to obtain a stable formulation if a pharmaceutically acceptable salt of caspofungin, for example caspofungin diacetate, is used.

Furthermore, the inventors have found that the compositions of the invention, when reconstituted with a solvent after lyophilization showed a significantly reduced number of sub-visible particles despite the absence of EDTA or related compounds. Even more surprisingly, the compositions of the invention showed a more reduced number of particles as compared to compositions containing EDTA sodium.

Thus the present invention provides a pharmaceutical composition comprising
a) a pharmaceutically acceptable salt of caspofungin,
b) an additional pH modifier in an amount below 0.3 mole equivalents of said salt of caspofungin, and
c) a pharmaceutically acceptable amount of an excipient, preferably a bulking agent, effective to form a lyophilized cake.

Preferably, the pharmaceutically acceptable salt of caspofungin is caspofungin diacetate and the bulking agent consists preferably of one or more bulking agents, also herein referred to as bulking sugars, preferably of mannitol, sucrose or a combination thereof.

In another aspect of the invention, the composition of the invention is substantially free of any additional pH modifier.

Additionally, the present invention provides a lyophilized powder obtainable by lyophilization of the pharmaceutical composition of the invention as described above. This lyophilized powder is suitable for reconstitution to form a liquid composition for parenteral, preferably intravenous, administration. Furthermore, the invention provides a pharmaceutical composition obtainable by reconstitution of said lyophilized powder with an aqueous solution, preferably with distilled and/or sterile water for injection, bacteriostatic water for injection optionally comprising methylparabene and/or propylparabene and/or 0.9% benzyl alcohol, or with normal saline or physiological saline, e.g. with a 0.9% solution of sodium chloride, or with a 0.45% or 0.225% solution of sodium chloride, or with Ringer's solution and/or Ringer's lactate solution.

The present invention further provides the use of the composition of the invention for the manufacture of a medicament, preferably an intravenous medicament, for the prevention and/or treatment of fungal infections or conditions caused by *Candida* sp. and/or by *Aspergillus* sp. and/or by *Pneumocystis jiroveci* in a mammal, preferably in a human.

The present invention additionally provides a process for preparing a pharmaceutical composition containing a pharmaceutically acceptable salt of caspofungin, which comprises the steps of
1) dissolving a bulking agent or a combination of bulking agents in water,
2) adding a pharmaceutically acceptable salt of caspofungin to the solution obtained in step 1) and dissolving it,
3) adding an additional pH modifier in an amount below 0.3 mole equivalents of said salt of caspofungin,
4) filtering the solution obtained in step 3),
5) freezing the solution obtained in step 4), and
6) freeze drying the frozen solution.

In another aspect, the present invention provides a process for preparing a pharmaceutical composition containing a pharmaceutically acceptable salt of caspofungin according to the process described above wherein step 3) is not comprised.

Additionally, the present invention provides compositions obtainable by the above described processes.

The pharmaceutical compositions of the invention are surprisingly stable, i.e. they contain a low number of total impurities being comparable to or even lower than the number observed in conventional compositions which contain additional substantial amounts of acetic acid or acetate buffers. Furthermore, the compositions of the invention show a reduced number of sub-visible particles as compared to acetate buffered conventional formulations and/or as compared to formulations containing EDTA. Advantageously, the compositions of the invention are straightforward to manufacture by more simple methods as compared to prior art processes.

BRIEF DESCRIPTION OF THE DRAWINGS

FIG. 1 shows total impurities of lyophilized Compositions 1 to 5 after reconstitution with ultrapure water according to the method described in Example 6. Ultrapure water is water which is obtained from a ultrapure water purification system, e.g. a Millipore Gradient A10 with UV-lamp and ultrafiltration. Ultrapure water has properties which are comparable to water for injection USP and Ph. Eur.

Composition 1 was prepared according to Example 1. This composition contained a substantial amount of additional acetate buffer and was prepared according to Example 1 of EP 0 904 098 B1. Composition 2 was manufactured according to Example 2. pH was adjusted with a low amount of acetic acid to pH 6.0 before lyophilization. Composition 3 was manufactured according to Example 3. pH was adjusted with a very low amount of acetic acid to pH 6.5 before lyophilization. Composition 4 was manufactured according to Example 4. Caspofungin diacetate was dissolved in an aqueous solution of mannitol and sucrose. No further pH-adjustment was performed. Composition 5 was manufactured according to Example 5. EDTA sodium dihydrate was added to result in a final concentration of 0.8 mg/ml before lyophilization. In FIG. 1 the Y-axis indicates total impurities in relative peak area in % as measured by HPLC. The X-axis indicates that the respective lyophilized composition has been stored at 5° C. for the indicated number of weeks.

FIG. 2 shows the results of an assay for caspofungin. Compositions 1 to 5 as defined in FIG. 1 were measured indirectly according to the method described in Example 7 after storage of the lyophilized composition at 2-8° C. for the number of weeks indicated by the X-axis. Y-axis indicates the amount of caspofungin found in the assay, expressed in relative peak area in % as measured by HPLC.

FIG. 3 shows the amounts of sub-visible particles having a size of >10 μm per vial of Compositions 1 to 5 as defined in FIG. 1. The number of particles was determined according to the method as described in Example 11 after storage of the lyophilized composition at about 5° C. for the number of weeks indicated by the X-axis. Measurement of particles was performed directly after reconstitution of the lyophilized samples. Y-axis indicates the number of sub-visible particles >10 μm in particles per vial.

FIG. 4 shows the amounts of sub-visible particles having a size of >25 μm per vial of Compositions 1 to 5 as described in FIG. 1. The number of particles was determined according to the method as described in Example 11 after storage of the lyophilized composition at 2-8° C. for the number of weeks indicated by the X-axis. Measurement of particles was performed directly after reconstitution of the lyophilized samples. Y-axis indicates the number of sub-visible particles >25 μm expressed in particles per vial. In FIGS. 1 to 4 a value of 0 on the X-axis means that analysis takes place directly after lyophilization.

FIG. 5 shows the X-ray powder diffraction (XRPD) pattern of crystalline caspofungin propionate being prepared as described in Example 17.

FIG. 6 shows the X-ray powder diffraction (XRPD) pattern of amorphous caspofungin propionate when comprised in a pharmaceutical composition which is prepared as described in Example 21.

In FIGS. 5 and 6, the abscissa shows values for theta/2 theta in degrees (CuKα-radiation), and the ordinate shows counts per second (cps).

DETAILED DESCRIPTION OF THE INVENTION

In one embodiment, the pharmaceutical composition of the invention comprises a pharmaceutically acceptable salt of caspofungin as the pharmaceutically active ingredient, pharmaceutically acceptable excipients which are suitable and/or effective to form a lyophilized cake, and an additional pH modifier in an amount below 0.3 mole equivalents of said pharmaceutically acceptable salt of caspofungin, preferably in an amount below 0.2 mole equivalents, more preferably below 0.1 mole equivalents.

In another embodiment, the pharmaceutical composition of the invention comprises a pharmaceutically acceptable salt of caspofungin as the pharmaceutically active ingredient and a pharmaceutically acceptable excipient which is suitable and/or effective to form a lyophilized cake, wherein said composition is substantially free or completely free of an additional pH modifier. "Substantially free" or "completely free" as herein used is understood to mean that no additional amount of a pH modifier, e.g. of acetic acid or of an acetate buffer, is added to form the composition of the invention. It is understood that said pharmaceutical compositions of the invention are also free of any additionally added buffering agent.

The term "caspofungin" as herein used means caspofungin free base, shown as the compound of formula I. Pharmaceutically acceptable salts of caspofungin have been, for example, described in EP 0 620 232. Pharmaceutically acceptable salts of caspofungin are the pharmaceutically active ingredient comprised in the compositions of the invention. The present invention also includes solvates and/or hydrates thereof.

The term "pharmaceutically acceptable salt of caspofungin" as used herein means non-toxic salts of caspofungin, and includes mono-, di- and tri-acid forms which are usually prepared by reacting the free base of caspofungin with a suitable organic or inorganic acid. Pharmaceutically acceptable salts suitable as acid addition salts as well as salts providing the anion of the quarternary salt are those from acids such as hydrochloric, hydrobromic, phosphoric, sulfuric, lactic, maleic, acetic, citric, tartaric, propionic, succinic, oxalic, malic, glutamic, pamoic acid and the like, and include other acids related to the pharmaceutically acceptable salts listed in Berge S. M., Bighley L. D., Monkhouse D. C.: "Pharmaceutical Salts", Journal of Pharmaceutical Sciences, 66 (1), 1977, pp. 1-19, and acids related to the counter ions in salt forms as listed in Strickley R. G.: "Parenteral Formulations of Small Molecules Therapeutics Marketed in the United States (1999)—Part I"; PDA Journal of Pharmaceutical Science & Technology, 53 (6), 1999, 324-349.

Preferably, the pharmaceutically acceptable salt of caspofungin is an acid addition salt with an organic acid which is selected from acetic, citric, tartaric, propionic, succinic, oxalic, malic, maleic, lactic, glutamic or pamoic acid. Most preferably, the pharmaceutically acceptable salt of caspofungin is caspofungin diacetate, propionate or lactate.

The excipient comprised in the composition of the invention is preferably a bulking agent which is effective to form a lyophilized cake. The term "bulking agent being effective to form a lyophilized cake" as herein used is understood to mean that this bulking agent adds bulk to a formulation or composition which results in a well-formed cake upon freeze drying, i.e. lyophilization. Such a bulking agent may also be referred to as a stabilizing agent or stabilizer, as it has also a stabilizing effect and additionally provides bulk to the lyophilized product or composition. Suitable bulking agents include, but are in no way limited to, polyhydric sugar alcohols, e.g. trihydric or higher alcohols such as glycerin, erythritol, arabitol, xylitol, sorbitol, and mannitol; lactose, sucrose, trehalose, dextrose, dextran, hydroxyethyl starch, ficoll or gelatin, or a mixture thereof, or others. Preferred bulking agents are mannitol and sucrose, or a mixture thereof.

The compositions of the invention may further comprise another, e.g. one or more pharmaceutically acceptable excipient, including diluents or carriers known in the art to be suitable for compositions intended for parenteral administration such as injectable formulations for intramuscular, subcutaneous, intravenous, intra-peritoneal or intramuscular administration. Such an excipient may include e.g. antioxidants, tonicity agents, preservatives, carbohydrates, waxes, water soluble and/or swelling polymers, hydrophilic or hydrophobic materials, gelatin, oils, solvents, water and the like.

Suitable solvents or diluents include but are not limited to aqueous solvents, preferably water e.g. distilled and/or sterile water for injection, bacteriostatic water for injection optionally comprising methylparabene and/or propylparabene and/or 0.9% benzyl alcohol, or normal saline or physiological saline, e.g. a 0.9% solution of sodium chloride, or a 0.45% or 0.225% solution of sodium chloride, or Ringer's solution and/or Ringer's lactate solution, wherein % are weight percent. These solvents and/or diluents may also be used for reconstitution of the compositions of the invention in the form of a lyophilized powder and/or for further diluting the reconstituted solution thereby obtained.

The term pH modifier as herein used is understood to mean a compound or substance suitable for adjusting the pH of liquid composition, e.g. of a solution, to a desired value such as to a pharmaceutically acceptable pH value, e.g. to a pH value of about 5 to about 8, e.g. of about 5 to about 7.5. pH modifiers are understood to include buffering agents or "buffers" or "buffering systems". The terms "buffering agents", "buffers" or "buffering systems" as herein used are understood to be interchangeable and to mean one or more pharmaceutically acceptable excipients that help to maintain the pH value of the liquid composition, e.g. of a solution, within a particular range specific to the buffering system. The term "pharmaceutically acceptable excipients" is understood to mean non-toxic excipients. Thus pH modifiers comprised in the compositions of the invention include, but are in no way limited to: organic or inorganic acids as herein described related to the formation of pharmaceutically acceptable salts of caspofungin, such as hydrochloric, hydrobromic, phosphoric, sulfuric, maleic, acetic, citric, tartaric, propionic, succinic, oxalic, lactic, malic, glutamic, pamoic acid and the like, other acids related to the pharmaceutically acceptable salts listed in Berge S. M. et al., 1977 (see above) and acids related to the counter ions in salt forms as listed in Strickley R. G., 1999 (see above); organic or inorganic bases such as sodium hydroxide, potassium hydroxide, ammonia, Tris(hydroxymethyl)-aminomethane, or buffering agents such as acetates, lactates, tartrates, citrates, phosphates, succinates, amino acids and the like, or those listed in Strickley R. G., 1999 (see above).

The compositions of the invention preferably comprise caspofungin calculated as caspofungin base in a concentration of about 0.1 mg/ml to about 500 mg/ml, such as about 10 mg/ml to about 200 mg/ml, preferably about 20 mg/ml to about 60 mg/ml, most preferably 42 mg/ml in case the composition is a liquid composition, i.e. additionally comprises e.g. water.

The excipients are preferably bulking agents which are present in an amount of about 10 mg/ml to about 200 mg/ml, preferably in an amount of about 40 mg/ml to about 60 mg/ml, more preferably in an amount of about 50 mg/ml. Preferably, the composition of the invention comprises a mixture of mannitol and sucrose wherein mannitol is present in amounts of about 10 mg/ml to about 200 mg/ml, preferably of about 10 mg/ml to about 30 mg/ml, most preferably of about 20 mg/ml, and sucrose is present in an amount of about 10 mg/ml to about 200 mg/ml, preferably of about 20 mg/ml to about 40 mg/ml, most preferably of about 30 mg/ml. The concentration in mg/ml mentioned above relates to the compositions of the invention in their liquid form, i.e. additionally comprising e.g. water.

The pH modifiers comprised in one preferred embodiment of the compositions of the invention are preferably used in a pharmaceutically acceptable amount which is necessary to adjust the pH of the composition of the invention in its liquid form, e.g. before lyophilization, to a value from about 5 to about 7, preferably from about 5.5 to about 6.5, more preferably to about 6.0. In case the composition of the invention is lyophilized as described below, the pH modifiers are preferably used in amounts which are effective to provide a pH value of about 5 to about 8, preferably of about 6 to about 7.5 in the liquid composition which is obtained after reconstitution of the lyophilized composition with a solvent, e.g. with water. The preferred pH modifier comprised of the compositions of the invention is acetic acid or hydrochloric acid. In said preferred embodiment of the invention the compositions comprise the additional pH modifier in an amount below 0.3 mole equivalents of the pharmaceutically acceptable said salt of caspofungin. The molar ratio of the caspofungin salt to the additional pH modifier is preferably more than 2:1, such as more than 3:1, preferably more than 4:1, 5:1, 8:1 or 10:1, in particular more than 25:1.

Thus, in one preferred aspect, the pharmaceutical composition of the invention comprises
a) about 0.1 mg/ml to about 500 mg/ml, e.g. about 10 mg/ml to about 200 mg/ml, preferably about 20 mg/ml to about 60 mg/ml, more preferably about 42 mg/ml of caspofungin calculated as caspofungin base,
b) a pharmaceutically acceptable amount of a pH modifier, preferably acetic acid, effective to provide a pH value of about 5 to about 7, preferably of about 5.5 to about 6.5, more preferably of about 6.0,
c) about 10 mg/ml to about 200 mg/ml, preferably about 40 mg/ml to about 60 mg/ml, more preferably about 50 mg/ml of an excipient being a bulking agent, preferably a mixture of bulking agents and/or bulking sugars, being effective to form a lyophilized cake, and water.

Preferably, the mixture of bulking sugars consists of a mixture of 20 mg/ml of mannitol and 30 mg/ml of sucrose.

Preferably, the composition of the invention comprises caspofungin diacetate in an amount of 46.6 mg/ml which corresponds to 42 mg/ml of caspofungin calculated as base. The molar ratio of the caspofungin salt to the additional pH modifier is preferably more than 2:1, such as more than 3:1, preferably more than 4:1, 5:1, 8:1 or 10:1, in particular more than 25:1.

In another preferred embodiment, the composition of the invention comprises the above described components a), c) and water, but is substantially free or completely free of any additional pH modifier.

The pH value of the liquid compositions described above is about 5 to about 7, preferably about 5.5 to about 6.5, more preferably of about 6.0.

The pharmaceutical compositions of the invention as described above, i.e. in their liquid form, e.g. in the form of aqueous solution, are preferably filled into vials in an amount of about 1 ml to about 3 ml, more preferably of about 1.25 ml or of about 1.75 ml per vial.

The pharmaceutical compositions of the invention as mentioned above are suitable to be lyophilized, e.g. may be lyophilized, preferably within the above mentioned vials, e.g. glass vials, according to methods described below in order to obtain a lyophilized powder. The composition of preferred embodiments of said lyophilized powder within one such vial expressed in mg of caspofungin calculated as base, of the pH modifier, preferably of acetic acid, if such additional pH modifier is present, and of the bulking agent, preferably being a mixture of mannitol and sucrose, may easily be calculated by multiplying the concentrations in mg/ml as indicated above by 1.25 or alternatively by 1.75. Thus, the present invention additionally provides a lyophilized powder obtainable by lyophilization of the above described pharmaceutical compositions which is suitable for reconstitution to form a liquid composition for parenteral, preferably intravenous, administration.

Preferred embodiments of the pharmaceutical compositions of the invention in form of a lyophilized powder comprise, and preferably consist of:
i) 58.28 mg Caspofungin diacetate corresponding to 52.5 mg caspofungin base, about 25 mg of mannitol, about 37.5 mg of sucrose, and additionally about e.g. 0.1 mg to 1.4 mg, preferably about 0.1 mg to about 0.7 mg acetic acid for pH adjustment; or
ii) 58.28 mg Caspofungin diacetate corresponding to 52.5 mg caspofungin base, about 25 mg of mannitol and about 37.5 mg of sucrose; or
iii) 81.59 mg Caspofungin diacetate corresponding to 73.5 mg caspofungin base, about 43.75 mg of mannitol, about 52.5 mg of sucrose, and additionally about e.g. 0.16 mg to about 2 mg, preferably about 0.16 mg to about 1 mg acetic acid for pH-adjustment; or iv) 81.59 mg Caspofungin diacetate corresponding to 73.5 mg caspofungin base, about 43.75 mg mannitol and about 52.5 mg sucrose.

The additional acetic acid present in preferred embodiments i) and iii) and being a pH modifier as described above is present in an amount which is effective to obtain a pH value of about 5 to about 8, preferably of about 6 to about 7.5, when the lyophilized powder of above is reconstituted with about 10.5 ml of an aqueous solvent or diluent as herein described.

The pharmaceutical compositions of the invention may thus be in a solid form, e.g. in the form of a powder, such as in the form of a lyophilized powder, e.g. in the form of a lyophilized cake, suitable for making a liquid for parenteral administration, such as injectable formulations for subcutaneous, intravenous, intra-peritoneal or intramuscular administration.

Thus, said lyophilized powder or cake, preferably obtained by lyophilization of the above described liquid pharmaceutical compositions may be reconstituted prior to parenteral administration by addition of a compatible diluent and/or solvent as herein described, e.g. by addition of an aqueous solution, preferably of distilled and/or sterile water for injection, bacteriostatic water for injection optionally comprising methylparabene and/or propylparabene and/or 0.9% benzyl alcohol, or of normal saline or physiological saline, e.g. of a 0.9% solution of sodium chloride, or of a 0.45% or 0.225% solution of sodium chloride, or of Ringer's solution and/or Ringer's lactate solution, e.g. by adding a suitable amount of said solvent or diluent directly into the vial, e.g. glass vial, used for lyophilization.

In a preferred aspect, the present invention thus provides a pharmaceutical composition obtainable by reconstituting the lyophilized powder according to the invention with an aqueous solution, preferably with 10.5 ml of said aqueous solution, more preferably of distilled and/or sterile water for injection, bacteriostatic water for injection optionally comprising methylparabene and/or propylparabene and/or 0.9% benzyl alcohol, or of normal saline or physiological saline, e.g. of a 0.9% solution of sodium chloride, or of a 0.45% or 0.225% solution of sodium chloride, or of Ringer's solution and/or Ringer's lactate solution. In a more preferred aspect, the present invention provides a pharmaceutical composition obtainable by reconstituting the above described preferred embodiments of the lyophilized powder according to the invention with 10.5 ml of the aqueous solutions as described above. For said preferred pharmaceutical compositions, the therein comprised concentrations in mg/ml of caspofungin calculated as caspofungin base, and of mannitol, sucrose and of the additional pH modifier, preferably of acetic acid, if present, may easily be calculated by dividing the corresponding amounts in mg figuring in the above described preferred embodiments of the lyophilized powder of the invention by 10.5.

The present invention therefore also provides an aqueous solution of a reconstituted lyophilized composition of the invention suitable for parenteral, preferably intravenous administration.

The pharmaceutical composition obtained after reconstitution of the lyophilized cake as described above has preferably a pH value of about 5 to about 8, preferably of about 6.0 to about 7.5.

Alternatively, the compositions of the invention comprising components a), c) and optionally b), and water as described above may exist in a liquid form, e.g. as a ready to use solution for parenteral administration, e.g. without being first lyophilized and subsequently reconstituted.

The pharmaceutical compositions of the invention are stable formulations and show a reduced number of sub-visible particles in case they are liquid formulations, such as in the form of a reconstituted lyophilized powder as herein described. Preferably, the pharmaceutical compositions of the invention in said liquid form have less than 500, preferably less than 300 sub-visible particles per vial, the particles having a size greater than 10 µm, the number of particles being determined according to USP 27, <788> Particulate matter in injections by light obscuration particle count test.

In one preferred embodiment, the compositions of the invention are prepared by a process comprising the following steps:

1) dissolving a bulking agent or a combination of bulking agents in water, 2) adding a pharmaceutically acceptable salt of caspofungin to the solution obtained in step 1) and dissolving it, 3) adding an additional pH modifier in an amount below 0.3 mole equivalents of said salt of caspofungin, preferably acetic acid or sodium hydroxide, to adjust the pH value of the solution obtained in step 2) to a value of about 5 to about 7, preferably of about 5.5 to about 6.5, more preferably to about 6.0, 4) filtering the solution obtained in step 3), filling the filtered solution into vials, preferably into lyophilization vials, and partially stoppering said vials, 5) freezing the solution obtained in step 4) in the vials in a freeze drier by adjusting the shelf temperature to about −50° C., and 6) freeze drying the frozen solution by adjusting the shelf temperature to about −40° C. and by adjusting an appropriate pressure to ensure sublimation of water from the frozen solution.

In another preferred embodiment, the compositions of the invention are prepared by a process comprising substantially the same steps as the process described above, but by omitting step 3) and thereby omitting the addition of an additional pH modifier. In this second process of the invention the solution obtained in step 2), i.e. after dissolving a bulking agent or a combination of bulking agents in water and adding a pharmaceutically acceptable salt of caspofungin to the resulting solution and dissolving it, said solution is directly filtered and filled in vials and further processed as described above in step 4), step 5) and step 6). Preferably, the pharmaceutically acceptable salt of caspofungin is caspofungin diacetate.

The acetic acid used in step 3) is suitably 1.25 N acetic acid. Optionally, water may be added to the solution obtained in step 3) of the first process or in step 2) of the second process described above to adjust to the desired total volume of the solution.

Filtering may be performed according or analogously to known methods, e.g. filtration may be performed using pharmaceutically acceptable filtration membranes having a pore size of not more than 0.22 µm.

The freeze dried solution obtained in step 6) may be further processed to obtain a pharmaceutical composition for parenteral administration. Such processing preferably comprises the step of completely stoppering the vials containing the lyophilized composition of the invention after completion of the freeze drying and storing them at a temperature of about 2° C. to about 8° C., e.g. at about 5° C., or under other suitable storage conditions.

The lyophilization or freeze drying is performed according or analogously to known methods. Preferably the freeze drying comprises a primary and a secondary drying, wherein the primary drying takes place at a temperature of about −40° C. shelf temperature, and the secondary drying takes place at about 15° C. shelf temperature. The complete drying cycle takes about 15 to 18 hours. The freeze drying may be performed in a Virtis freeze dryer, e.g. available as Virtis Advantage II, according to known methods and using an appropriate pressure, e.g. a pressure below 0.12 mbar.

Therefore, the present invention also provides a pharmaceutical composition obtainable, preferably obtained by one of the above described processes.

The lyophilized composition may be diluted, e.g. reconstituted before administration to a mammal, e.g. to a human subject, with a suitable diluent or solvent as herein described to obtain a final concentration of caspofungin calculated as caspofungin base, e.g. of about 5 mg/ml or 7 mg/ml. The reconstituted solution may be withdrawn from the vial and may be transferred into an infusion bag for further administration by intravenous infusion. In such way, the reconstituted solution may be further diluted with an appropriate solvent or diluent as herein described to provide a solution suitable for infusion to a patient. Preferred solvents or diluents are distilled and/or sterile water for injection, bacteriostatic water for injection optionally comprising methylparabene and/or propylparabene and/or 0.9% benzyl alcohol, or normal saline or physiological saline, e.g. a 0.9% solution of sodium chloride, or a 0.45% or 0.225% solution of sodium chloride, or Ringer's solution and/or Ringer's lactate solution. Dilution of the pharmaceutical composition of the invention in the form of a reconstituted solution as described above may be performed by diluting 7 ml to 10 ml, preferably 7 ml or 10 ml, of the reconstituted solution with the herein described diluents to a total volume of about 100 ml to about 300 ml, preferably of about 110 ml to about 250 ml or about 260 ml. Dilution of the reconstituted solution should be performed in such way as to provide a pharmaceutical composition comprising a pharmaceutically acceptable and therapeutically effective amount of caspofungin calculated as base. The term "therapeutically effective" as herein used is understood to mean to provide a desired therapeutical, prophylactical, physiological and/or pharmacological and/or antimicrobial, e.g. antibacterial or antifungal, and/or anti-protozoal effect. The dosage scheme for prevention and/or treatment of the herein mentioned diseases will be easily determined by a skilled physician, e.g. as described below.

The compositions of the inventions may be administered to a mammal, preferably to a human subject and/or patient for preventing and/or treating infectious diseases caused by fungi or protozoes.

Thus the present invention provides the use of a composition of the invention as a medicament for preventing and/or treating mycotic infections in mammals, preferably in humans, particularly those caused by *Candida* species such as *C. albicans, C. tropicalis, C. krusei, C. glabrata* and *C. pseudotropicalis*, and by *Aspergillus* species such as *A. fumigatus, A. flavus* and *A. niger*. Compositions of the invention are also effective against putatively Amphotericin B and Fluconazole-resistant *Candida* strains. Furthermore, the compositions of the invention may be used for the prevention and/or treatment of pneumonia caused by *Pneumocystis jiroveci* to which immuno-suppressed patients, e.g. those suffering of AIDS, are especially susceptible. *Pneumocystis jiroveci* was previously classified as *Pneumocystis carinii* and as a protozoon, but is now considered a fungus.

Preferably the composition of the invention comprises the caspofungin as pharmaceutically active ingredient in a therapeutically effective amount. If administered intravenously, the most preferred doses of active ingredient will range from about 1.67 µg/kg/minute to about 33 µg/kg/minute with an infusion rate of about 200 ml/hour. For such administration, the composition of the invention should have 0.025 mg/ml to 0.5 mg/ml of active ingredient, i.e. caspofungin base, based on a 50 kg patient, as is described in EP 0 904 098 B1.

The pharmaceutical compositions of the invention, in particular those being substantially free or completely free of both any additional pH modifier and any additional buffering agent, offer several advantages as compared to known caspofungin formulations.

The reduced number of sub-visible particles in the liquid compositions of the invention, particularly in those being substantially free or completely free of any additional pH modifier, is a surprising feature of the present invention. Normally one would expect e.g. from U.S. Pat. No. 6,900,184, or from WO 02/41919 A1, that the presence of a particulate formation inhibitor such as EDTA sodium would be needed to effectively reduce sub-visible particles of solutions for injection as EDTA is expected to complex ions in solution, e.g. calcium ions released from the glass vials, which may potentially form precipitates with e.g. hydroxides or silicates. Unexpectedly, the compositions of the invention show a more expressed reduction of said sub-visible particles despite the absence of any such particulate formation inhibitor. This is particularly seen with the compositions of the invention which are substantially free of any additional pH modifier.

Thus the compositions of the invention preferably have less than 500, preferably less than 300 sub-visible particles per vial, the particles having a size greater than 10 µm, the number of particles being determined according to USP 27, <788> Particulate matter in injections: Light Obscuration Particle Count Test. Consequently the compositions of the invention advantageously provide increased safety to the patients who receive said compositions parenterally, e.g. intravenously, by reducing a potential risk of embolia due to sub-visible particles.

As a further advantage, the compositions of the invention provide stable compositions showing a low amount of total impurities whereof the main degradation product of caspofungin—herein also referred to as CAF-42—which results from splitting off ethylene diamine is also significantly reduced particularly in the compositions of the inventions being substantially free of any additional buffering agents or of any pH modifying agents (see Example 12 and Table 5). The high stability of the compositions of the invention is also shown by its high contents of active ingredient maintained during storage. This favorable stability of the compositions of the invention, in particular of those compositions being free of any additional pH modifier, is obtained without the necessity of adding any additional buffering agent which generally requires 2 steps of pH adjustment. Thus, the time for preparing the liquid forms of such pharmaceutical compositions—which are suitable for lyophilization as herein described—is estimated to be reduced by at least 10%. Compositions of the invention comprising an additional pH modifier in a small amount, namely below 0.3 mole equivalents of the salt of caspofungin comprised in the composition, are also highly stable formulations the preparation of which requires only 1 step of pH adjustment. Consequently, the compositions of the invention are straightforward to manufacture by more simple methods as compared to prior art processes.

As an additional advantage, the pharmaceutical compositions of the invention, in particular those being free of any additional pH modifier, show higher purity in terms of less formation of impurities such as e.g. CAF-Dimer 1 as compared to conventional caspofungin formulations comprising an additional acetate buffer (see Example 13).

The present inventors have also found that the pharmaceutical compositions of the invention, in particular in the form of a lyophilized powder which has been reconstituted with water for injection or with physiological saline, show good stability in terms of maintaining the pH at about the same value during a storage of 2 days at 25° C. despite the absence of any additional buffer, e.g. acetate buffer. It has furthermore been observed that the reconstituted solutions according to the invention, in particular those being substantially free or completely free of both any additional pH modifier and of any additional buffering agent, show surprisingly good stability also in terms of low amounts of total impurities and/or of the main degradation product CAF-42 and/or of the impurity CAF-Dimer 1.

The inventors have also found a novel salt of a compound of formula I, namely an acid addition salt with propionic acid which is suitable for the pharmaceutical compositions as herein described.

Thus, in a further aspect, the present invention provides a novel salt of caspofungin, being a compound of formula I,

I

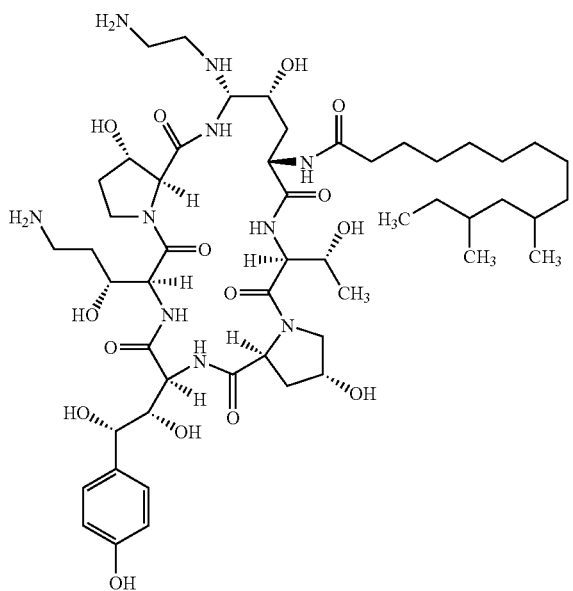

in the form of an acid addition salt with propionic acid. Said novel salt is also referred to as caspofungin propionate.

In a preferred aspect, caspofungin propionate according to the invention comprises caspofungin of formula I and propionic acid in a molar ratio of about 1:1 to about 1:3, more preferably of about 1:1.5 to about 1:2.5, e.g. of 1:1.8 to 1:2.2, most preferably of about 1:2. The latter may be defined as caspofungin dipropionate and may correspond to a compound of formula II.

Thus, in a more preferred aspect the present invention provides caspofungin propionate of formula II

II

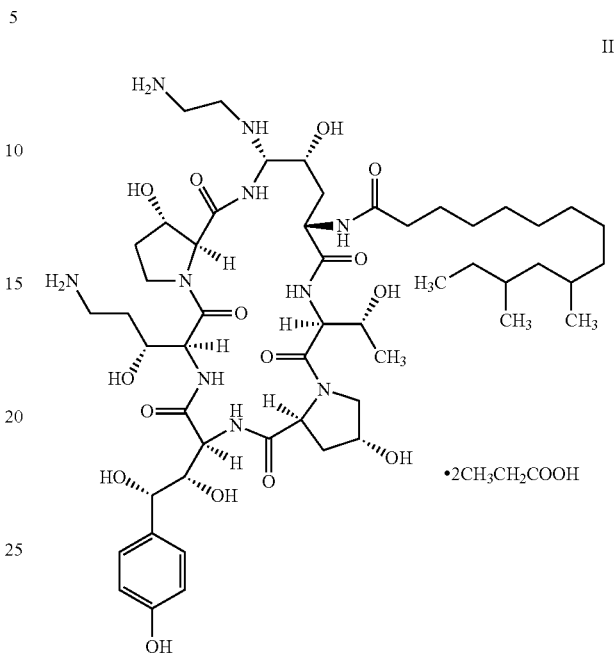

·2CH$_3$CH$_2$COOH

The compound of formula II is also referred to as caspofungin dipropionate.

The present invention additionally provides caspofungin of formula I in the form of its acid addition salt with propionic acid and/or caspofungin propionate as described above preferably in a crystalline form or in an amorphous form.

The terms "caspofungin propionate" as herein used are understood to mean the novel salt of caspofungin according to the invention and are understood to include "a compound of formula I in the form of an acid addition salt with propionic acid", in particular wherein the molar ratio of caspofungin of formula I to propionic acid may be about 1:1 to about 1:3, "a compound of formula II" and "caspofungin dipropionate". The term "caspofungin propionic acid adduct" as herein used should be understood to mean an acid addition salt of caspofungin with propionic acid.

Caspofungin propionate according to the present invention, in particular caspofungin dipropionate in crystalline form may be characterized by the $^1$H-NMR data (CD$_3$OD, 300 MHz) and/or by the $^{13}$C-NMR data (CD$_3$OD, 75 MHz) as shown in Table 10 below. Caspofungin dipropionate has been prepared as described in Example 17.

TABLE 10

| $^1$H-NMR data and $^{13}$C-NMR data of caspofungin dipropionate | | | | |
|---|---|---|---|---|
| | | CAF dipropionate of formula II $^{13}$C-NMR data | CAF dipropionate of formula II $^1$H-NMR data | |
| | | [PPM] | [PPM] | [PPM] |
| 1 | C=O | 173.2 | | |
| 2 | CH—N | 50.2 | 4.51 | m |

TABLE 10-continued

¹H-NMR data and ¹³C-NMR data of caspofungin dipropionate

| | | CAF dipropionate of formula II ¹³C-NMR data [PPM] | CAF dipropionate of formula II ¹H-NMR data [PPM] | | | |
|---|---|---|---|---|---|---|
| 3 | CH₂ | 34.8 | 2.05 | m | 1.84 | m |
| 4 | CH—O | 69.1 | 4.03 | m | | |
| 5 | CH—N | 63.4 | 4.69 | d | | |
| 7 | C=O | 172.7 | | | | |
| 8 | CH—N | 68.3 | 4.20 | d | | |
| 9 | CH—O | 74.1 | 4.32 | m | | |
| 10 | CH₂ | 33.6 | 2.25 | m | 2.00 | m |
| 11 | CH₂—N | 46.0 | 3.85 | t | | |
| 13 | C=O | 167.9 | | | | |
| 14 | CH—N | 55.1 | 4.94 | d | | |
| 16 | C=O | 171.7 | | | | |
| 17 | CH—N | 55.0 | 4.34 | m | | |
| 19 | C=O | 172.5 | | | | |
| 20 | CH—N | 61.7 | 4.57 | m | | |
| 21 | CH₂ | 37.5 | 2.45 | m | 2.07 | m |
| 22 | CH—O | 70.3 | 4.58 | m | | |
| 23 | CH₂—N | 56.1 | 4.00 | m | 3.80 | m |
| 25 | C=O | 171.8 | | | | |
| 26 | CH—N | 57.3 | 5.00 | d | | |
| 28 | CH—O | 67.2 | 4.62 | m | | |
| 29 | CH₃ | 18.9 | 1.20 | d | | |
| 30 | CH—O | 71.1 | 4.08 | m | | |
| 31 | CH₂ | 29.9 | 2.04 | m | 1.85 | m |
| 32 | CH₂—N | 38.0 | 3.07 | t | | |
| 34 | CH—O | 76.3 | 4.24 | dd | | |
| 35 | CH—O | 74.6 | 4.34 | m | | |
| 36 | =Cq | 132.0 | | | | |
| 37 | =CH | 128.6 | 7.14 | m | | |
| 38 | =CH | 115.2 | 6.77 | m | | |
| 39 | =Cq | 157.5 | | | | |
| 40 | =CH | 115.2 | 6.77 | m | | |
| 41 | =CH | 128.6 | 7.14 | m | | |
| 43 | C=O | 175.3 | | | | |
| 44 | CH₂ | 35.9 | 2.26 | m | | |
| 45 | CH₂ | 26.1 | 1.61 | m | | |
| 46 | CH₂ | 29.3 | 1.3 | m | | |
| 47 | CH₂ | 29.6 | 1.3 | m | | |
| 48 | CH₂ | 29.8 | 1.3 | m | | |
| 49 | CH₂ | 30.2 | 1.3 | m | | |
| 50 | CH₂ | 27.0 | 1.31 | m | | |
| 51 | CH₂ | 37.1 | 1.33 | m | 1.08 | m |
| 52 | CH | 30.2 | 1.50 | m | | |
| 53 | CH₂ | 44.9 | 1.26 | m | 0.94 | m |
| 54 | CH | 31.9 | 1.44 | m | | |
| 55 | CH₂ | 29.4 | 1.3 | m | 1.12 | m |
| 56 | CH₃ | 10.6 | 0.9 | t | | |
| 57 | CH₃ | 19.7 | 0.88 | d | | |
| 58 | CH₃ | 19.2 | 0.88 | d | | |
| 59 | CH₂—N | 43.2 | 2.91 | m | 2.81 | m |
| 60 | CH₂—N | 39.5 | 2.99 | m | | |
| PRA | C=O | 182.2 | | | | |
| PRA | CH₂ | 30.6 | 2.19 | q | | |
| PRA | CH₃ | 10.1 | 1.11 | t | | |

In Table 10:
PRA = propionic acid;
[PPM] = unit of chemical shift in parts per million;
m = multiplet,
d = doublet,
dd = doublet of doublet,
t = triplet,
q = quartet.

Numbers indicate the numbers in the structural formula IV which are the basis for signal assignment:

IV

[Structural formula of caspofungin dipropionate with numbered atoms, and 2× propionic acid (CH₃CH₂COOH)]

Caspofungin propionate according to the present invention, in particular in crystalline form, may be characterized by the triplet at about 1.11 ppm originating from the methyl group of propionic acid and the quartet at about 2.19 ppm originating from the methylene group of propionic acid in its ¹H-NMR spectrum as shown in Table 10.

Caspofungin propionate, in particular in crystalline form may also be characterized by the signals at about 10.1, 30.6 and 182.2 ppm originating from the methyl group, the methylene group and the carboxyl group of propionic acid, respectively, in its ¹³C-NMR spectrum as shown in Table 10.

In another aspect, caspofungin propionate, in particular caspofungin dipropionate in crystalline form may be characterized by an X-ray powder diffraction (XRPD) pattern substantially in accordance with FIG. 5. Caspofungin dipropionate has been prepared as described in Example 17 where also the method of XRPD-measurement is described.

In still another aspect, caspofungin propionate, in particular caspofungin dipropionate in crystalline form may be characterized by an X-ray powder diffraction (XRPD) pattern having intensity peaks at values expressed in 2-theta degrees of about 2.92, 5.04, 5.88, 9.02 and 10.23.

Alternatively, caspofungin propionate, in particular caspofungin dipropionate in crystalline form may be characterized by an X-ray powder diffraction (XRPD) pattern having intensity peaks at values expressed in 2-theta degrees of 2.9±0.2, 5.0±0.2, 5.9±0.2, 9.01±0.2 and 10.2±0.2, e.g. of 2.9±0.1, 5.0±0.1, 5.9±0.1, 9.0±0.1 and 10.2±0.1.

Crystalline caspofungin propionate, in particular crystalline caspofungin dipropionate, may further be characterized in that crystals are prisms which can form agglomerates, and which are easily flowable and freely soluble in water. Thus, the present invention provides crystalline caspofungin propionate being easy to handle, e.g. during preparation of pharmaceutical compositions comprising caspofungin propionate as active ingredient. Crystalline caspofungin propionate has the advantage that it is more stable than the amorphous form.

In a preferred embodiment, crystalline caspofungin propionate is characterized by a defined molar ratio of caspofungin of formula I to propionic acid of about 1:1 to about 1:3, preferably of about 1:1.5 to about 1:2.5, e.g. of 1:1.8 to 1:2.2, more preferably of about 1:2. The latter may be defined as caspofungin dipropionate and may correspond to a compound of formula II. Said defined molar ratio of caspofungin of formula I to propionic acid—in addition to the above mentioned easy flowability and free solubility in water—makes crystalline caspofungin propionate, in particular crystalline caspofungin dipropionate, particularly advantageous for use in the preparation of a pharmaceutical composition as herein described.

Crystalline caspofungin propionate, in particular caspofungin dipropionate, according to the present invention shows a high degree of crystallinity. The present invention therefore also relates in a preferred aspect to a crystalline form of caspofungin propionate, in particular of caspofungin dipropionate, comprising less than 5%, in particular less than 1% of amorphous caspofungin propionate, in particular of amorphous caspofungin dipropionate. In another preferred aspect, the present invention relates to a crystalline form of caspofungin propionate, in particular of caspofungin dipropionate, being substantially or completely free of any amorphous caspofungin propionate, in particular of amorphous caspofungin dipropionate. Crystalline caspofungin propionate, in particular crystalline caspofungin dipropionate being substantially or completely free of amorphous caspofungin propionate and/or amorphous caspofungin dipropionate, shows good stability.

Amorphous caspofungin propionate, in particular amorphous caspofungin dipropionate, is freely soluble in water and is easy to handle, e.g. during preparation of pharmaceutical compositions comprising caspofungin propionate as active ingredient. In a preferred embodiment, amorphous caspofungin propionate according to the invention is characterized by a molar ratio of caspofungin of formula I and propionic acid of about 1:1 to about 1:3, preferably of about 1:1.5 to about 1:2.5, e.g. of 1:1.8 to 1:2.2, more preferably of about 1:2. The latter may be defined as caspofungin dipropionate and may correspond to a compound of formula II.

In another preferred embodiment, amorphous caspofungin propionate, in particular caspofungin dipropionate, shows a defined molar ratio of caspofungin of formula I and propionic acid in the range as described above. Said amorphous caspofungin propionate having said defined molar ratio may be obtained by conversion of crystalline caspofungin propionate, in particular of crystalline caspofungin dipropionate, into an amorphous form thereof by dissolving the crystalline caspofungin propionate or crystalline caspofungin dipropionate in water and by subsequently lyophilizing the obtained solution according to known methods. Consequently, amorphous caspofungin propionate, in particular caspofungin dipropionate, having said defined molar ratio is particularly suitable for the preparation of pharmaceutical compositions as herein described.

Amorphous caspofungin propionate, in particular dipropionate, according to the present invention may be prepared without detectable traces of crystalline caspofungin propionate, in particular of crystalline caspofungin dipropionate. The present invention therefore relates—in a preferred embodiment—to an amorphous form of caspofungin propionate, in particular of caspofungin dipropionate, comprising less than 5%, in particular less than 1% of crystalline caspofungin propionate, in particular of crystalline caspofungin dipropionate. In another preferred aspect, the present invention relates to an amorphous form of caspofungin propionate, in particular of caspofungin dipropionate, being substantially or completely free of any crystalline caspofungin propionate, in particular of crystalline caspofungin dipropionate.

Caspofungin propionate according to the invention, e.g. in crystalline or in amorphous form, may further comprise residual solvents, e.g. residual organic solvents such as a $C_1$-$C_4$-alcohol, e.g. methanol or ethanol, or an acetic acid $C_1$-$C_4$-alkyl ester, e.g. ethyl acetate, and/or water. In one aspect, caspofungin propionate may contain up to about 10%, e.g. up to 10%, such as up to about 5%, e.g. up to 5% of residual organic solvents, and/or up to about 10%, e.g. about 1% to about 10%, such as about 2% to about 8% of water, wherein % are weight percent. The water content may be measured according to known methods, e.g. according to Karl Fischer. The residual organic solvents may be measured by known methods, e.g. by head space gas chromatography GC using a DB-Wax capillary column. Without wishing to be bound by theory, the present inventors believe that the above mentioned amounts of residual organic solvents, e.g. of ethanol or ethyl acetate, and/or of water within the crystalline form of caspofungin propionate might have a stabilizing effect.

Therefore, in one aspect the present invention provides caspofungin propionate, e.g. in crystalline form or in amorphous form, comprising up to about 10%, e.g. up to 10%, such as up to about 5%, e.g. up to 5% of residual organic solvents, preferably of a $C_1$-$C_4$-alcohol, e.g. methanol or ethanol, or of an acetic acid $C_1$-$C_4$-alkyl ester, e.g. ethyl acetate, and/or up to about 10%, e.g. about 1% to about 10%, such as about 2% to about 8%, e.g. 2% to 8% of water, wherein % are weight percent.

In another embodiment of the invention, caspofungin propionate, e.g. in crystalline form or in amorphous form, may be substantially free or completely free of residual organic solvents.

Excess residual organic solvents and/or water may be removed from crystalline caspofungin propionate according to the invention by drying methods as known, e.g. by drying in vacuo, or by e.g. applying a nitrogen flow according to known methods. Alternatively, residual organic solvents may be removed from crystalline caspofungin propionate by passing humid nitrogen of about 20% to about 55%, e.g. of about 30% to about 50% relative humidity, at a temperature of about 0° C. to about 30° C., e.g. of about 10° C. to about 25° C., e.g. at room temperature, such as at 25° C.±5° C., through the solid crystalline product obtained by the processes herein described to obtain crystalline caspofungin propionate having a content of residual solvents in accordance with the ICH guidelines (International Conference on Harmonization of Technical Requirements for Registration of Pharmaceuticals for Human Use, ICH Harmonized Tripartite Guideline, Impurities: Guideline for Residual Solvents, Q3C(R3), Current Step 4 version, Parent Guideline dated 17 Jul. 1997). Alternatively, residual solvents may be removed from crystalline caspofungin propionate by exposing said crystalline caspofungin propionate to a relative humidity of about 20% to about 80%, preferably of about 30% to about 50%, at a temperature of about 0° C. to about 30° C., e.g. of about 10° C. to about 25° C., e.g. at room temperature, such as at 25° C.±5° C., to obtain crystalline caspofungin propionate having a content of residual solvents in accordance with the above mentioned ICH guidelines. Optionally, crystalline caspofungin propionate as obtained after application of the humid nitrogen flow or after exposure to humidity as described above may further be converted to an amorphous form by dissolution in water and lyophilization as described above in order to provide amorphous caspofungin propionate, in particular amorphous caspofungin dipropionate, being substantially or completely free of residual organic solvents and being particularly suitable for the preparation of pharmaceutical compositions as herein described.

The present invention further provides a pharmaceutical composition comprising caspofungin propionate according to the invention, e.g. in crystalline or amorphous form, and optionally additionally one or more pharmaceutically acceptable excipients known in the art. In one preferred aspect, the pharmaceutical composition according to the invention comprises caspofungin propionate in crystalline form or in amorphous form and additionally one or more of the herein described pharmaceutically acceptable excipients.

The amorphous form of caspofungin propionate according to the invention—when it is comprised in a pharmaceutical composition as herein described—shows no distinct peaks in its XRPD pattern which is depicted in FIG. 6 wherein the pharmaceutical composition comprising caspofungin propionate, more particularly, caspofungin dipropionate, has been prepared as described in Example 21; the method of XRPD-measurement is described in Example 17.

In one preferred aspect, the pharmaceutical composition according to the invention is in a liquid form, more preferably in the form of an aqueous solution. The pharmaceutical compositions of the invention may e.g. exist as a ready to use solution, e.g. aqueous solution, for parenteral administration.

In another preferred aspect, the pharmaceutical composition of the invention is in a solid form, preferably in the form of a lyophilized powder.

In one preferred embodiment, the pharmaceutical composition of the invention comprises caspofungin propionate, e.g. caspofungin dipropionate, according to the invention as pharmaceutically active ingredient, and a pharmaceutically acceptable excipient, preferably a bulking agent being suitable and/or effective to form a lyophilized cake, and an additional buffer, preferably a propionate buffer as defined below, which is effective to provide a pharmaceutically acceptable pH value, e.g. to provide a pH value in the range of about 5 to about 8, e.g. of about 5.5 to about 7.5, such as about 5.5 to about 7.0, e.g. of about 5.5 to about 6.5, e.g. of about 6.0. The buffer, preferably the propionate buffer, contributes to the buffer capacity of the pharmaceutical composition.

In another preferred embodiment, the pharmaceutical composition of the invention comprises caspofungin propionate, e.g. caspofungin dipropionate, according to the invention as pharmaceutically active ingredient, and a pharmaceutically acceptable excipient, preferably a bulking agent being suitable and/or effective to form a lyophilized cake, and an additional pH modifier, e.g. propionic acid, which is effective to adjust the pH value to a pharmaceutically acceptable pH value as herein described. The term pH modifier as herein used is defined above.

In another preferred embodiment, the pharmaceutical composition of the invention comprises caspofungin propionate, e.g. caspofungin dipropionate, according to the invention as pharmaceutically active ingredient and a pharmaceutically acceptable excipient which is suitable and/or effective to form a lyophilized cake, wherein said pharmaceutical composition is substantially free of an additional buffer or pH modifier. "Substantially free" as herein used is understood to mean that no additional amount of a buffer or of a pH modifier, e.g. of a propionate buffer or of propionic acid, is added to form the pharmaceutical composition of the invention.

A preferred excipient of the pharmaceutical composition of the invention is a bulking agent which is effective to form a lyophilized cake; such preferred bulking agents are described above.

The compositions of the invention may further comprise one or more additional pharmaceutically acceptable excipients, including diluents or carriers known in the art to be suitable for compositions intended for parenteral administration such as injectable formulations for intramuscular, subcutaneous, intravenous, intra-peritoneal or intramuscular administration. Suitable excipients as well as suitable solvents and/or diluents are described above. Preferred solvents and/or diluents used for reconstitution of the pharmaceutical compositions of the invention in the form of a lyophilized powder and/or for further diluting the reconstituted solution thereby obtained are: distilled and/or sterile water for injection, bacteriostatic water for injection optionally comprising methylparabene and/or propylparabene and/or 0.9% benzyl alcohol, or normal saline or physiological saline, e.g. a 0.9% solution of sodium chloride, or a 0.45% or a 0.225% solution of sodium chloride, or Ringer's solution and/or Ringer's lactate solution.

A preferred composition of the invention is an aqueous solution comprising caspofungin propionate, in particular caspofungin dipropionate, in a concentration corresponding to about 0.1 mg/ml to about 500 mg/ml, e.g. about 10 mg/ml to about 200 mg/ml, preferably about 20 mg/ml to about 60 mg/ml, more preferably about 22 mg/ml to about 45 mg/ml, most preferably to about 25 mg/ml, to about 30.6 mg/ml or to about 42 mg/ml of caspofungin calculated as base.

More preferably, the above described aqueous solution also comprises bulking agents which are present in a concentration of about 10 mg/ml to about 200 mg/ml, preferably in concentration of about 20 mg/ml to about 60 mg/ml, e.g. of about 25 mg/ml to about 55 mg/ml, more preferably of about 30 mg/ml to about 52 mg/ml, most preferably of about 32.5 mg/ml, of about 39.4 mg/ml or of about 50 mg/ml. Preferably, the bulking agents are a mixture of mannitol and sucrose, preferably in a molar ratio of from about 1:2 to about 2:1, more preferably of about 1:1.

In one preferred aspect, the invention thus relates to a composition in the form of an aqueous solution comprising
I) caspofungin propionate, e.g. caspofungin dipropionate, in a concentration corresponding to about 0.1 mg/ml to about 500 mg/ml, e.g. of about 10 mg/ml to about 200 mg/ml, preferably about 20 mg/ml to about 60 mg/ml, more preferably about 22 mg/ml to about 45 mg/ml, most preferably of about 25 mg/ml, of about 30.6 mg/ml or of about 42 mg/ml of caspofungin calculated as caspofungin base,
II) about 10 mg/ml to about 200 mg/ml, preferably about 20 mg/ml to about 60 mg/ml, e.g. of about 25 mg/ml to about 55 mg/ml, more preferably about 30 mg/ml to about 52 mg/ml, most preferably of about 32.5 mg/ml, of about 39.4 mg/ml or of about 50 mg/ml of an excipient being a bulking agent, preferably a mixture of bulking agents, being effective to form a lyophilized cake, and
III) optionally a pharmaceutically acceptable amount of a buffer, preferably propionate buffer, or of a pH modifier, preferably propionic acid, effective to provide a pH value of about 5 to about 7, preferably of about 5.5 to about 6.5, more preferably of about 6.0, and water.

Preferably, the bulking agent used in component II) is a mixture of bulking agents, more preferably a mixture of mannitol and sucrose, preferably in a molar ratio of from about 1:2 to about 2:1, more preferably of about 1:1.

Thus, in one preferred embodiment, the composition of the invention in the form of an aqueous solution comprises components I) and II) and component III) wherein a buffer, preferably a propionate buffer, is present in a pharmaceutically acceptable amount, and water. To provide a pharmaceutically acceptable amount of a propionate buffer effective to achieve the desired pH value, suitable amounts of propionic acid and sodium hydroxide, or of propionic acid and sodium propionate, or of sodium propionate and a strong anorganic acid, e.g. HCl, can be used. Preferably, the propionate buffer present in component III) is prepared by adding a suitable amount of propionic acid and of NaOH to the above described aqueous solution to provide a pH value of about 5 to about 7, preferably of about 5.5 to about 6.5, more preferably of about 6.0. The preparation of the aqueous solution comprising the additional buffer, preferably propionate buffer, may be performed analogously to, e.g. according to processes as described e.g. in European Patent EP 0 904 098 B1, or e.g. as described in Example 20. The buffer, preferably propionate buffer, is preferably present in the range of about 1 mmol/l to about 200 mmol/l, more preferably in the range of about 12.5 mmol/l to about 100 mmol/l, most preferably in the range of about 15 mmol/l to about 50 mmol/l, e.g. of about 17 mmol/l to about 25 mmol/l. The buffer is intended to add some further buffer capacity to the I composition of the invention.

In another preferred embodiment, the composition of the invention in the form of an aqueous solution comprises the above described components I) and II), and component III) wherein a pH modifier, preferably propionic acid, is present in a pharmaceutically acceptable amount which is effective to provide a pH value, e.g. which is necessary to adjust a pH value of about 5 to about 7, preferably of about 5.5 to about 6.5, more preferably of about 6.0, and water. Preferred pH modifiers used in component III) are propionic acid or hydrochloric acid, more preferably, propionic acid. Preferably, the additional pH modifier is present in an amount above or below 0.3 mole equivalents of caspofungin propionate, in particular caspofungin propionate according to the invention. In another preferred aspect, the molar ratio of caspofungin propionate, in particular caspofungin dipropionate to the additional pH modifier is more than 2:1, such as more than 3:1, preferably more than 4:1, 5:1, 8:1 or 10:1, in particular more than 25:1. The pH modifier, preferably propionic acid, is preferably present in the range of about up to 5 mmol/l, e.g. of about 2 mmol/l to about 4 mmol/l, preferably of about 3 mmol/l. The preparation of the aqueous solution comprising the additional pH modifier, preferably propionic acid, may be performed analogously to, e.g. according to the herein described processes, e.g. in Examples 2 and 3, or as described in Example 21.

In still another preferred embodiment, the composition of the invention in the form of an aqueous solution comprises the above described components I) and II) and water, but is substantially free and/or completely free of any additional buffer or any additional pH modifier. Said compositions being free of any additional buffer or any additional pH modifier may be prepared by processes analogous to, e.g. according to the herein described processes, e.g. in Example 4 or 14, or e.g. as described in Example 22.

Particularly preferred embodiments of the composition of the invention comprise xi) caspofungin propionate, in particular caspofungin dipropionate, in a concentration of about 28.4 mg/ml corresponding to about 25 mg/ml of caspofungin calculated as base, and about 32.5 mg/ml of a bulking agent being a mixture of about 13 mg/ml of mannitol and of about 19.5 mg/ml of sucrose, and water, and optionally about 17 mmol/l of a propionate buffer or 1.8 mmol/l of propionic acid as pH modifier; or xii) caspofungin propionate, in particular caspofungin dipropionate, in a concentration of about 34.8 mg/ml corresponding to about 30.6 mg/ml of caspofungin calculated as base, and about 39.4 mg/ml of a bulking agent being a mixture of about 15.8 mg/ml of mannitol and of about 23.6 mg/ml of sucrose, and water, and optionally about 20 mmol/l of a propionate buffer or about 2.2 mmol/l of propionic acid as pH modifier; or xiii) caspofungin propionate, in particular caspofungin dipropionate, in a concentration of about 47.7 mg/ml corresponding to about 42 mg/ml of caspofungin calculated as base, and about 50 mg/ml of a bulking agent being a mixture of about 20 mg/ml of mannitol and of about 30 mg/ml of sucrose, and water, and optionally about 25 mmol/l of a propionate buffer or about 3 mmol/l of propionic acid as pH modifier.

The optionally present buffer, preferably propionate buffer, or pH modifier is effective to provide a pH value of the liquid compositions described above of preferably about 5 to about 7, e.g. about 5.5 to about 6.5, more preferably of about 6.0.

The compositions of the invention in the form of an aqueous solution as described above are preferably filled into vials in a volume of about 0.1 ml to about 15 ml, e.g. of about 0.3 ml to about 9 ml, preferably of about 0.1 ml to about 3.3 ml, more preferably of about 0.3 ml to about 3 ml per vial,

- e.g. in a volume preferably of about 0.476 ml per vial of composition xiii) to obtain a pharmaceutical composition comprising caspofungin propionate, e.g. caspofungin dipropionate, in an amount corresponding to about 20 mg of caspofungin calculated as caspofungin base, or
- e.g. in a volume preferably of about 1.25 ml per vial of composition xiii), or alternatively in a volume preferably of about 1.714 ml per vial of composition xii), or alternatively in a volume preferably of about 2.1 ml per vial of composition xi), to obtain a pharmaceutical composition comprising caspofungin propionate, e.g. caspofungin dipropionate, in an amount corresponding to about 52.5 mg of caspofungin calculated as caspofungin base; or
- e.g. in a volume preferably of about 1.75 ml per vial of composition xiii), or alternatively in a volume preferably of about 2.4 ml per vial of composition xii), or alternatively in a volume preferably of about 2.94 ml per vial of composition xi) to obtain a pharmaceutical composition comprising caspofungin propionate, e.g. caspofungin dipropionate, in an amount corresponding to about 73.5 mg of caspofungin calculated as caspofungin base; or
- e.g. in a volume preferably of about 0.25 ml per vial of composition xiii), or alternatively in a volume preferably of about 0.343 ml per vial of composition xii), or alternatively in a volume preferably of about 0.42 ml per vial of composition xi), to obtain a pharmaceutical composition comprising caspofungin propionate, e.g. caspofungin dipropionate, in an amount corresponding to about 10.5 mg of caspofungin calculated as caspofungin base, or
- e.g. in a volume preferably of about 8.75 ml per vial of composition xiii), or alternatively in a volume preferably of about 12 ml of composition xii), or alternatively in a volume preferably of about 14.7 ml of composition xi) to obtain a pharmaceutical composition comprising caspofungin propionate, e.g. caspofungin dipropionate, in an amount corresponding to about 367.5 mg of caspofungin calculated as caspofungin base.

The compositions of the invention in the form of an aqueous solution, e.g. as compositions xi), xii) or xiii) may also be filled into vials in volumes in ml being different from those described above so that further pharmaceutical compositions may be obtained whereof the content in caspofungin propionate, e.g. caspofungin dipropionate, calculated as caspofungin base per vial may easily be calculated.

The pharmaceutical compositions obtained by filling suitable amounts of the compositions of the invention in the form of an aqueous solution, e.g. of compositions xi), xii) or xiii) as described above into vials preferably comprise a unit dose of caspofungin dipropionate of about 11.93 mg to about 417.3 mg corresponding to about 10.5 mg to about 367.5 mg, preferably to about 50 mg to about 77 mg, more preferably to about 52.5 mg or to about 73.5 mg of caspofungin calculated as caspofungin base. Said pharmaceutical compositions may be used to provide a unit dose of about 10 mg, about 350 mg, preferably of about 50 mg or about 70 mg, respectively, of caspofungin calculated as caspofungin base, because they include each a 5% overfill. These pharmaceutical compositions may be administered parenterally as such, e.g. as a ready-to-use solution, and/or may be administered parenterally after further dilution with the herein described solvents and/or diluents.

In a preferred aspect, the compositions of the invention in the form of an aqueous solution, e.g. suitable amounts of compositions xi), xii) or xiii) as described above, are filled into vials, e.g. glass vials, and are subsequently lyophilized, i.e. freeze-dried according to known methods, to obtain pharmaceutical compositions according to the invention in the form of a lyophilized powder.

Lyophilization may e.g. be performed as follows, e.g. analogously, e.g. according to the method described in Example 20; the vials containing suitable amounts of an aqueous solution, e.g. of compositions xi), xii) or xiii), are partially stoppered and lyophilized until a cake is formed at the bottom of the vial by using e.g. a freeze drier as commercially available as Christ Epsilon 2-6 D™ freeze-drier. In brief, primary drying is performed at a temperature of about −40° C. and in a vacuum of about 0.04 mbar for about 960 minutes. Secondary drying is performed at +15° C. within about 3 hours at a vacuum of about 0.011 mbar. Process parameters may be adapted e.g. for varying filling heights of the vials, and process time for individual steps of freeze-drying may be adjusted to ensure complete drying of compositions according to known methods.

Thus, present invention further provides—in a preferred aspect—a pharmaceutical composition in a solid form, e.g. in the form of a powder, preferably in the form of a lyophilized powder which is obtainable, preferably obtained, by lyophilization of the compositions of the invention in the form of an aqueous solution, preferably of the compositions xi), xii) or xiii), as described above. Said lyophilized powder is suitable for making a liquid for parenteral administration, such as injectable formulations for subcutaneous, intravenous, intraperitoneal or intramuscular administration, preferably intravenous administration.

Preferably, the pharmaceutical composition in the form of a lyophilized powder comprises caspofungin dipropionate in a unit dose of about 11.93 mg to about 417.3 mg, preferably of about 56.8 mg to about 87.43 mg, more preferably of about 59.61 mg or of about 83.46 mg corresponding to about 10.5 mg to about 367.5 mg, preferably to about 50 mg to about 77 mg, more preferably to about 52.5 mg or to about 73.5 mg, respectively, of caspofungin calculated as caspofungin base. Said pharmaceutical compositions may be used to provide a unit dose of about 10 mg to about 350 mg, preferably of about 50 mg or about 70 mg, respectively, of caspofungin calculated as caspofungin base, after reconstitution with 10.5 ml of the herein described solvents, e.g. aqueous solvents, and withdrawal of 10 ml of the reconstituted solution for administration to a patient and/or for further dilution, because they include each a 5% overfill.

In one preferred embodiment, the lyophilized powder according to the invention comprises a unit dose of caspofungin dipropionate of about 56.78 mg to about 62.45 mg, preferably of about 59.61 mg corresponding to about 50 mg to about 55 mg, preferably to about 52.5 mg of caspofungin calculated as base, respectively, and further comprises about 23.8 mg to about 28.7 mg, preferably about 25 mg to about 28 mg of mannitol and about 35.6 mg to about 43 mg, preferably about 37 mg to about 41 mg of sucrose, and additionally comprises about 2.23 mg to about 2.75 mg, preferably about 2.3 mg to about 2.6 mg of propionic acid. Said additional propionic acid—which is part of the additional propionate buffer—is present in an amount which is effective to provide a pH value of about 5 to about 8, preferably of about 6.0 to about 7.5, when the lyophilized powder of above is reconstituted with about 10.5 ml of an aqueous solvent or diluent as herein described. The lyophilized powder described above thus comprises about 9 mg to about 10.2 mg, preferably of about 9.4 mg to about 9.7 mg of total propionic acid which—additionally to the above described amounts of propionic acid derived from propionate buffer—also includes the propionic acid derived from the propionate counter ion of caspofungin dipropionate comprised in the pharmaceutical composition. Specifically preferred embodiments of the lyophilized powder comprise 59.61 mg caspofungin dipropionate corresponding to 52.5 mg of caspofungin calculated as base, and further comprise a mixture of 25 mg of mannitol and 37.5 mg of sucrose, or of 27 mg of mannitol and of 40.5 mg of sucrose, or of 27.3 mg of mannitol and of 40.95 mg of sucrose, and additionally comprise 2.31 mg or 2.58 mg or 2.5 mg, respectively, of propionic acid being part of the propionate buffer. Said specifically preferred embodiments thus comprise 9.43 mg or 9.62 mg or 9.7 mg, respectively, of total propionic acid including 7.11 mg of propionic acid derived from the propionate counter ion of caspofungin dipropionate.

In another preferred embodiment, the lyophilized powder according to the invention comprises a unit dose of caspofungin dipropionate of about 56.78 mg to about 62.45 mg, preferably of about 59.61 mg corresponding to about 50 mg to about 55 mg, preferably to about 52.5 mg of caspofungin calculated as base, respectively, and further comprises about 23.8 mg to about 28.7 mg, preferably about 25 mg to about 28 mg of mannitol and about 35.6 mg to about 43 mg, preferably about 37 mg to about 41 mg of sucrose, and additionally comprises about 0.12 mg to about 0.45 mg, preferably about 0.19 mg to about 0.39 mg of propionic acid. Said additional propionic acid is a pH modifier as described above and is present in an amount which is effective to obtain a pH value of about 5 to about 8, preferably of about 6.0 to about 7.5, when the lyophilized powder of above is reconstituted with about 10.5 ml of an aqueous solvent or diluent as herein described. The lyophilized powder described above thus comprises about 6.9 mg to about 7.9 mg, preferably of about 7.3 mg to about 7.5 mg of total propionic acid which—additionally to the above described amounts of propionic acid being the pH modifier—also include the propionic acid derived from the counter ion of caspofungin dipropionate comprised in the pharmaceutical composition. Specifically preferred embodiments of the lyophilized powder comprise 59.61 mg caspofungin dipropionate corresponding to 52.5 mg of caspofungin calculated as base, and further comprise a mixture of 25 mg of mannitol and 37.5 mg of sucrose, or of 27 mg of mannitol and of 40.5 mg of sucrose, or of 27.3 mg of mannitol and of 40.95 mg of sucrose, and additionally comprise about 0.29 mg or about 0.31 mg or about 0.32 mg of propionic acid being the pH modifier. Said specifically preferred embodiments thus comprise about 7.40 mg or about 7.43 mg or about 7.44 mg, respectively, of total propionic acid including 7.11 mg of propionic acid derived from the propionate counter ion of caspofungin dipropionate.

In still another preferred embodiment, the lyophilized powder according to the invention comprises a unit dose of caspofungin dipropionate of about 56.78 mg to about 62.45 mg, preferably of about 59.61 mg corresponding to about 50 mg to about 55 mg, preferably to about 52.5 mg of caspofungin calculated as base, respectively, and further comprises about 23.8 mg to about 28.7 mg, preferably about 25 mg to about 28 mg of mannitol and about 35.6 mg to about 43 mg, preferably about 37 mg to about 41 mg of sucrose, but does not comprise any additional propionic acid being a pH modifier or part of a propionate buffer. The lyophilized powder described above comprises about 6.75 mg to about 7.47 mg, preferably about 7.11 mg of total propionic acid which is—in its entirety—derived from the propionate counter ion of caspofungin dipropionate comprised in the pharmaceutical composition. Specifically preferred embodiments of the lyophilized powder comprise 59.61 mg caspofungin dipropionate corresponding to 52.5 mg of caspofungin calculated as base, and further comprise a mixture of 25 mg of mannitol and 37.5 mg of sucrose, or of 27 mg of mannitol and of 40.5 mg of sucrose, or of 27.3 mg of mannitol and of 40.95 mg of sucrose. Said specifically preferred embodiments also comprise 7.11 mg of total propionic acid being derived from the propionate counter ion of caspofungin dipropionate.

In a further preferred embodiment, the lyophilized powder according to the invention comprises a unit dose of caspofungin dipropionate of about 79.5 mg to about 87.43 mg, preferably of about 83.46 mg corresponding to about 70 mg to about 77 mg, preferably to about 73.50 mg of caspofungin calculated as base, respectively, and further comprising about 33.3 mg to about 40.4 mg, preferably about 35 mg to about 38.5 mg of mannitol and about 49.4 mg to about 60.4 mg, preferably about 52 mg to about 57.5 mg of sucrose, and additionally comprising about 3.05 mg to about 3.85 mg, preferably about 3.24 mg to about 3.64 mg of propionic acid wherein said propionic acid is part of the additional propionate buffer and is present in an amount which is effective to provide a pH value of about 5 to about 8, preferably of about 6.0 to about 7.5, when the lyophilized powder of above is reconstituted with about 10.5 ml of an aqueous solvent or diluent as herein described. The lyophilized powder described above thus comprises about 12.54 mg to about 14.28 mg, preferably of about 13.20 mg to about 13.60 mg of total propionic acid which also includes the propionic acid derived from the propionate counter ion of caspofungin dipropionate comprised in the pharmaceutical composition. Specifically preferred embodiments of the lyophilized powder comprise 83.46 mg of caspofungin dipropionate corresponding to 73.5 mg of caspofungin calculated as base, and further comprise a mixture of 35 mg of mannitol and 52.5 mg of sucrose, or of 37.8 mg of mannitol and of 56.71 mg of sucrose, or of 38.22 mg of mannitol and of 57.33 mg of sucrose, and additionally comprise 3.24 mg or of 3.5 mg or of 3.62 mg, respectively, of propionic acid being part of the additional propionate buffer. Said specifically preferred embodiments thus comprise a total amount of propionic acid of 13.2 mg or 13.47 mg or 13.58 mg, respectively, including 9.96 mg of propionic acid derived from the propionate counter ion of caspofungin dipropionate.

In another preferred embodiment, the lyophilized powder according to the invention comprises a unit dose of caspofungin dipropionate of about 79.5 mg to about 87.43 mg, preferably of about 83.46 mg corresponding to about 70 mg to about 77 mg, preferably to about 73.50 mg of caspofungin calculated as base, respectively, and further comprises about 33.3 mg to about 40.4 mg, preferably about 35 mg to about 38.5 mg of mannitol and about 49.4 mg to about 60.4 mg, preferably about 52 mg to about 57.5 mg of sucrose, and additionally comprises about 0.11 mg to about 1.07 mg, preferably about 0.34 mg to about 0.54 mg of propionic acid. Said additional propionic acid being a pH modifier is present in an amount which is effective to obtain a pH value of about 5 to about 8, preferably of about 6.0 to about 7.5, when the lyophilized powder of above is reconstituted with about 10.5 ml of an aqueous solvent or diluent as herein described. The lyophilized powder described above thus comprises about 9.7 mg to about 11.5 mg, preferably of about 10.3 mg to about 10.5 mg of total propionic acid which—additionally to the above described amounts of propionic acid being the pH modifier—also include the propionic acid derived from the propionate counter ion of caspofungin dipropionate comprised in the pharmaceutical composition. Specifically preferred embodiments of the lyophilized powder comprise 83.46 mg of caspofungin dipropionate corresponding to 73.5 mg of caspofungin calculated as base, and further comprise a mixture of 35 mg of mannitol and 52.5 mg of sucrose, or of 37.8 mg of mannitol and of 56.71 mg of sucrose, or of 38.22 mg of mannitol and of 57.33 mg of sucrose, and additionally comprise about 0.40 mg or about 0.44 mg or about 0.45 mg, respectively, of propionic acid being a pH modifier. Said specifically preferred embodiments thus comprise about 10.37 mg or about 10.40 mg or about 10.41 mg, respectively, of total propionic acid including 9.96 mg of propionic acid derived from the propionate counter ion of caspofungin dipropionate.

In still another preferred embodiment, the lyophilized powder according to the invention comprises a unit dose of caspofungin dipropionate of about 79.5 mg to about 87.43 mg, preferably of about 83.46 mg corresponding to about 70 mg to about 77 mg, preferably to about 73.50 mg of caspofungin calculated as base, respectively, and further comprises about 33.3 mg to about 40.4 mg, preferably about 35 mg to about 38.5 mg of mannitol and about 49.4 mg to about 60.4 mg, preferably about 52 mg to about 57.5 mg of sucrose, but does not comprise any additional propionic acid being a pH modifier or part of a propionate buffer. The lyophilized powder described above comprises about 9.5 mg to about 10.5 mg, preferably about 10 mg of total propionic acid which is—in its entirety—derived from the propionate counter ion of caspofungin dipropionate comprised in the pharmaceutical composition. Specifically preferred embodiments of the lyophilized powder comprise 83.46 mg of caspofungin dipropionate corresponding to 73.5 mg of caspofungin calculated as base, and further comprise a mixture of 35 mg of mannitol and 52.5 mg of sucrose, or of 37.8 mg of mannitol and of 56.71 mg of sucrose, or of 38.22 mg of mannitol and of 57.33 mg of sucrose. Said specifically preferred embodiments also comprise 9.96 mg of total propionic acid being derived from the propionate counter ion of caspofungin dipropionate.

In a further preferred embodiment, the lyophilized powder according to the invention comprises a unit dose of caspofungin dipropionate of about 11.36 mg to about 12.5 mg, preferably of about 11.9 mg corresponding to about 10 mg to about 11 mg, preferably to about 10.5 mg of caspofungin calculated as base, and about 4.75 mg to about 5.78 mg, preferably about 5 mg to about 5.5 mg of mannitol and about 7.1 mg to about 8.6 mg, preferably about 7.5 mg to about 8.2 mg of sucrose, and optionally additionally comprises about 0.44 mg to about 0.56 mg, preferably about 0.46 mg to about 0.53 mg of propionic acid being part of an additional propionate buffer and being present in an amount which is effective to provide a pH value of about 5 to about 8, preferably of about 6.0 to about 7.5, when the lyophilized powder of above is reconstituted with about 10.5 ml of an aqueous solvent or diluent as herein described. If the lyophilized powder described above contains the additional propionate buffer, it thus comprises about 1.8 mg to about 2.05 mg, preferably about 1.9 mg to about 1.95 mg of total propionic acid which also includes the propionic acid derived from the propionate counter ion of caspofungin dipropionate comprised in the pharmaceutical composition. In case the lyophilized powder of above does not contain an additional propionate buffer, it comprises about 1.36 mg to about 1.49 mg, preferably about 1.42 mg of total propionic acid which is—in its entirety—derived from the propionate counter ion of caspofungin dipropionate comprised in the pharmaceutical composition. Specifically preferred embodiments of the lyophilized powder of above comprise 11.92 mg caspofungin dipropionate corresponding to 10.5 mg of caspofungin calculated as base, and further comprise a mixture of 5 mg of mannitol and 7.5 mg of sucrose, or of 5.4 mg of mannitol and of 8.11 mg of sucrose, or of 5.46 mg of mannitol and of 8.19 mg of sucrose, and optionally additionally comprise 0.46 mg or 0.5 mg or 0.52 mg, respectively, of propionic acid being part of the additional propionate buffer. In case these specifically preferred embodiments contain the propionate buffer, they comprise 1.89 mg or 1.92 mg or 1.94 mg, respectively, of total propionic acid including propionic acid derived from the propionate counter ion of caspofungin dipropionate. In case these specifically preferred embodiments do not contain a propionate buffer, they comprise 1.42 mg of total propionic acid derived from the counter ion of caspofungin dipropionate.

In a further preferred embodiment, the lyophilized powder according to the invention comprises a unit dose of caspofungin dipropionate of about 397.4 mg to about 438.3 mg, preferably about 417.3 mg corresponding to about 350 mg to about 386 mg, preferably to about 367.5 mg of caspofungin calculated as base, and about 166 mg to about 200 mg, preferably about 175 mg to about 192 mg of mannitol and about 250 mg to about 300 mg, preferably about 263 mg to about 287 mg of sucrose, and optionally additionally about 15.27 mg to about 19.1 mg, preferably about 16.2 mg to about 18.2 mg of propionic acid being part of an additional propionate buffer and being present in an amount which is effective to provide a pH value of about 5 to about 8, preferably of about 6.0 to about 7.5, when the lyophilized powder of above is reconstituted with about 10.5 ml of an aqueous solvent or diluent as herein described. If the lyophilized powder of above contains the additional propionate buffer, it thus comprises about 62.7 mg to about 71.4 mg, preferably about 66 mg to about 68 mg of total propionic acid which also includes the propionic acid derived from the propionate counter ion of caspofungin dipropionate comprised in the pharmaceutical composition. In case the lyophilized powder of above does not contain an additional propionate buffer, it comprises about 47.43 mg to about 52.3 mg, preferably about 49.8 mg of total propionic acid which is—in its entirety—derived from the propionate counter ion of caspofungin dipropionate comprised in the pharmaceutical composition. Specifically preferred embodiments of the lyophilized powder comprise 417.30 mg caspofungin dipropionate corresponding to 367.5 mg of caspofungin calculated as base, and further comprise a mixture of 175 mg of mannitol and 262.5 mg of sucrose, or of 189 mg of mannitol and of 283.56 mg of sucrose, or of 191.1 mg of mannitol and of 286.65 mg of sucrose, and optionally additionally comprise 16.19 mg or 17.52 mg or 18.08 mg, respectively, of propionic acid being part of the additional propionate buffer. In case these specifically preferred embodiments contain the propionate buffer, they comprise 65.99 mg or 67.33 mg or 67.88 mg, respectively, of total propionic acid including propionic acid derived from the propionate counter ion of caspofungin dipropionate. In case these specifically preferred embodiments do not contain a propionate buffer, they comprise 49.8 mg of total propionic acid derived from the counter ion of caspofungin dipropionate.

Further preferred embodiments of the lyophilized powder of above comprising a unit dose of caspofungin dipropionate about 11.9 mg or of about 417.3 mg corresponding to about 10.5 mg or to about 367.5 mg of caspofungin calculated as base, comprise propionic acid as a pH modifier—instead of the additional propionate buffer—in amounts effective to obtain a pH value of about 5 to about 8, preferably of about 6.0 to about 7.5, when the lyophilized powder of above is reconstituted with about 10.5 ml of an aqueous solvent or diluent as herein described. Said corresponding amounts of propionic acid being a pH modifier may easily be calculated analogously to the amounts given e.g. for the other preferred embodiments described above, e.g. containing caspofungin dipropionate corresponding to about 50 mg to about 55 mg of caspofungin calculated as base.

The pharmaceutical composition in the form of a lyophilized powder according to the invention as described above may be reconstituted prior to parenteral administration by addition of a compatible diluent and/or solvent as herein described, e.g. with an aqueous solution, e.g. by adding a suitable amount of said solvent or diluent directly into the vial, e.g. glass vial, used for lyophilization.

The present invention therefore provides a pharmaceutical composition obtainable, preferably obtained, by reconstituting the lyophilized powder according to the invention as described above with an aqueous solution, preferably with water, e.g. with distilled and/or sterile water for injection, bacteriostatic water for injection optionally comprising methylparabene and/or propylparabene and/or 0.9% benzyl alcohol, or with normal saline or physiological saline, e.g. with a 0.9% aqueous solution of sodium chloride, or with a 0.45% or 0.225% solution of sodium chloride, or with Ringer's solution and/or Ringer's lactate solution, thus forming an aqueous solution of a reconstituted lyophilized composition of the invention suitable for parenteral administration.

In a preferred aspect, the present invention provides a pharmaceutical composition obtainable by reconstituting the lyophilized powder according to the invention with 10.5 ml of an aqueous solution, preferably of the preferred solutions described above. In a more preferred aspect, the present invention provides a pharmaceutical composition obtainable by reconstituting the above described preferred embodiments and specifically preferred embodiments of the lyophilized powder according to the invention with 10.5 ml of an aqueous solution, preferably of water, e.g. distilled and/or sterile water for injection, bacteriostatic water for injection optionally comprising methylparabene and/or propylparabene and/or 0.9% benzyl alcohol, or of normal saline or physiological saline, e.g. of a 0.9% aqueous solution of sodium chloride, or of a 0.45% or 0.225% solution of sodium chloride, or of Ringer's solution and/or Ringer's lactate solution. For said preferred pharmaceutical compositions, the concentrations in mg/ml of caspofungin dipropionate calculated as caspofungin base, and of mannitol, sucrose and propionic acid therein comprised may easily be calculated by dividing the corresponding amounts in mg figuring in the above described preferred and specifically preferred embodiments of the lyophilized powder of the invention by 10.5.

The pharmaceutical composition of the invention in the form of a reconstituted solution as described above may be further diluted with an appropriate solvent or diluent, preferably with the preferred solvents and/or diluents as herein described to provide a solution suitable for infusion to a patient. Dilution of the pharmaceutical composition of the invention in the form of a reconstituted solution as described above may be performed by diluting 7 ml to 10 ml, preferably 7 ml or 10 ml, of the reconstituted solution with the herein described diluents to a total volume of about 100 to about 300 ml, preferably of about 110 ml to about 250 ml or 260 ml. Dilution of the reconstituted solution should be performed in such way as to provide a pharmaceutical composition comprising a pharmaceutically acceptable and therapeutically effective amount of caspofungin propionate, in particular of caspofungin dipropionate. The term "therapeutically effective" as well as the dosage scheme for prevention and/or treatment of the herein mentioned diseases are defined above.

The pharmaceutical composition after reconstitution of the lyophilized powder according to the invention as described above has preferably a pH value of about 5 to about 8, preferably of about 6.0 to about 7.5.

In one preferred aspect, the pharmaceutical compositions of the invention are suitable for parenteral administration as herein described. Without wishing to be bound by theory, the present inventors believe that the pharmaceutical compositions of the invention enhance the stability of caspofungin propionate, e.g. caspofungin dipropionate therein comprised.

In an even more preferred aspect, the present invention provides pharmaceutical compositions comprising caspofungin propionate for parenteral administration showing high purity. Said high purity is observed e.g. in pharmaceutical compositions being a reconstituted solution of a lyophilized powder as herein described, e.g. in Examples 20 to 28, as which show only a low content in total impurities, e.g. of less than 1.5%, preferably of not more than 1.3%, e.g. of not more than 1%, e.g.—of not more than 0.7% to about 0.9% of total impurities as measured by HPLC according to known methods, and/or which exhibit only a low amount of subvisible particles >25 µm, e.g. of less than 30, preferably of less than 25, e.g. of not more than 18 subvisible particles >25 µm per vial, and/or subvisible particles >10 µm, e.g. of less than 650, preferably of less than 620, e.g. of not more than 615 subvisible particles >10 µm per vial, as measured according to known methods. Measurement of total impurities by HPLC and/or determination of subvisible particles by the method according to USP 29, <788> Particulate matter in injections: Light Obscuration Particle Count test, are described in Example 20 and/or in Examples 23 to 28.

Additionally, the pharmaceutical compositions of the invention include pharmaceutical compositions suitable for oral, topical, nasal and suppository administration. Pharmaceutical compositions for oral administration may be liquid or solid compositions. The above mentioned compositions may accordingly comprise pharmaceutically acceptable excipients suitable for the above mentioned kinds of administration. Such excipients and the way how to use them for preparing said compositions are known.

In one preferred aspect, crystalline caspofungin propionate, e.g. crystalline caspofungin dipropionate, is used for the preparation of the above mentioned pharmaceutical compositions.

In another preferred aspect, amorphous caspofungin propionate, e.g. amorphous caspofungin dipropionate, as obtained by conversion of crystalline caspofungin propionate or of crystalline caspofungin dipropionate, involving dissolution in water and lyophilization as herein described, is used for the preparation of the above mentioned pharmaceutical compositions. More preferably, the crystalline caspofungin propionate or crystalline caspofungin dipropionate used for the conversion, is treated with humid nitrogen or is alternatively exposed to humidity to remove residual organic solvents before being converted as described above.

The present invention also provides processes to prepare caspofungin propionate.

Therefore, in one embodiment, the present invention relates to a process for preparing caspofungin propionate which comprises the following steps:

A) dissolving caspofungin in the form of a salt, preferably caspofungin diacetate, in a suitable solvent being a mixture of an organic solvent and water, preferably being a mixture of a $C_1$-$C_4$-alcohol and water, B) purifying the mixture obtained in step A) by reversed phase HPLC in the presence of propionic acid, and C) lyophilizing the fractions obtained in step B).

The organic solvent used in step A) is preferably a $C_1$-$C_4$-alcohol, e.g. methanol or ethanol or the like, more preferably methanol. Thus a preferred solvent being a mixture of an organic solvent and water used in step A) is a mixture of methanol and water.

In the above described process, caspofungin in the form of a salt, e.g. caspofungin diacetate, may be prepared in situ by dissolving caspofungin as a base in a mixture of a suitable organic solvent, e.g. of a $C_1$-$C_4$-alcohol, e.g. methanol or ethanol, preferably methanol, and water by addition of a suitable acid, such as an inorganic or organic acid, preferably an organic acid, more preferably propionic acid.

Step B), i.e. purifying the mixture obtained in step A) by reversed phase HPLC in the presence of propionic acid to obtain rich cut fractions, may be performed by applying a mixture of acetonitrile and water and propionic acid to elute the product from the reversed phase HPLC column. The mixture of acetonitrile and water may be a 22 acetonitrile/78 water (v/v) mixture comprising about 0.25% of propionic acid, e.g. about 0.05%-2.0%, e.g. 0.1%-1.0%, such as 0.2%-0.5% of propionic acid wherein % are weight percentages. Reversed phase HPLC may be performed according to known methods and using e.g. a C-8 or C-18 reversed phase adsorbent and column, e.g. such as commercially available from YMC Europe GmbH.

Step C), i.e. lyophilizing the fractions obtained in step B) may be performed analogous, e.g. according to known methods.

The product obtained in step C), i.e. the lyophilized product is caspofungin propionate according to the invention, particularly in its amorphous form, as e.g. prepared in Example 17 where it is described as caspofungin propionic acid adduct.

In another embodiment, the present invention relates to a process for preparing caspofungin propionate which comprises—in addition to steps A) to C) as described above—the following further steps of:

D) dissolving the lyophilized product obtained in step C) in a mixture of an organic solvent and water, preferably in a mixture of a $C_1$-$C_4$-alcohol and water, E) adding propionic acid and subsequently an acetic acid $C_1$-$C_4$-alkyl ester, preferably ethyl acetate to obtain a suspension, and F) isolating caspofungin propionate from the suspension obtained in step E).

The organic solvent used in step D) is preferably a $C_1$-$C_4$-alcohol, e.g. methanol or ethanol or the like, more preferably ethanol. Thus a preferred solvent being a mixture of an organic solvent and water is a mixture of ethanol and water.

The acetic acid $C_1$-$C_4$-alkyl ester used in step E) may be methyl acetate, ethyl acetate, n-propyl acetate or iso-propyl acetate, n-butyl acetate or iso-butyl acetate, preferably ethyl acetate.

Step E), i.e. adding propionic acid and subsequently an acetic acid $C_1$-$C_4$-alkyl ester, preferably ethyl acetate, to obtain a suspension, may e.g. be performed as follows: add propionic acid and subsequently a first portion of ethyl acetate to the mixture obtained in step D) and stir at room temperature, i.e. at about 25° C.±5° C., until crystallization starts, continue to stir for e.g. about 1 hour until a seed bed is established, and subsequently add a second portion of ethyl acetate over a prolonged period of time, e.g. over about 3 to about 5 hours, e.g. over about 4 hours, and age the resulting crystal suspension e.g. for about 1 hour. Optionally, the solution may be seeded.

Step F), i.e. isolation of caspofungin propionate from the suspension obtained in step E), may be performed according to known methods, e.g. by filtration of the crystal suspension to recover the crystalline solid which is dried e.g. in vacuo at ambient temperature, e.g. at room temperature, such as at about 25° C.±5° C., to obtain caspofungin propionate, e.g. caspofungin dipropionate. Optionally, the solid obtained by filtration may be washed, e.g. with a mixture of ethanol, water and ethyl acetate, before drying. The drying procedure may also be performed by applying a nitrogen flow according to known methods. Alternatively, humid nitrogen, e.g. of 20% to 55%, such as of 30% to 50% relative humidity, may be passed through the crystalline solid recovered by filtration to remove residual organic solvents as described above. This treatment may control the residual water content of caspofungin propionate and reduce the formation of unwanted degradation products.

Preferably, caspofungin propionate obtained in step F) is caspofungin dipropionate, more preferably of formula II, in its crystalline form, as e.g. prepared in Example 17.

In another embodiment, the present invention provides a process for preparing caspofungin propionate comprising the following steps:

A') dissolving caspofungin in the form of a salt, preferably caspofungin diacetate, in a suitable solvent, preferably in water, B') adjusting the pH value of the solution obtained in step A') to about 9.0 to obtain a suspension, C') filtering the suspension obtained in step B'), and optionally washing the resulting product with water, D') dissolving the product obtained in step C') in an organic solvent, preferably a $C_1$-$C_4$-alcohol, containing propionic acid to obtain a solution, E') filtering the solution obtained in step D') and adding an acetic acid $C_1$-$C_4$-alkyl ester, preferably ethyl acetate, to obtain a suspension, and F') isolating caspofungin propionate from the suspension obtained in step E').

The organic solvent used in step D') is preferably a $C_1$-$C_4$-alcohol, e.g. methanol or ethanol or the like, more preferably ethanol.

The acetic acid $C_1$-$C_4$-alkyl ester used in step E') may be methyl acetate, ethyl acetate, n-propyl acetate or iso-propyl acetate, n-butyl acetate or iso-butyl acetate, preferably ethyl acetate.

Step E') may e.g. be performed as follows: add a first portion of ethyl acetate to the solution obtained in step D') and stir at room temperature, i.e. at about 25° C.±5° C., until crystallization starts, continue to stir for about 1 hour until a seed bed is established and subsequently add a further portion of ethyl acetate over a prolonged period of time, e.g. over about 3 to about 5 hours, e.g. over about 4 hours, and age the resulting crystal suspension e.g. for about 1 hour. Optionally, the solution may be seeded.

Step F'), i.e. isolation of caspofungin propionate from the suspension obtained in step E'), may be performed according to known methods, e.g. by filtration and drying analogously, e.g. analogous to, e.g. according to step F) as described above.

Preferably, caspofungin propionate obtained in step F') is caspofungin dipropionate, e.g. of formula II, in its crystalline form, as e.g. prepared in Example 18.

In still another embodiment, the present invention provides a process for preparing caspofungin propionate comprising the following steps:

A") dissolving or suspending a compound of formula III or an acid addition salt thereof:

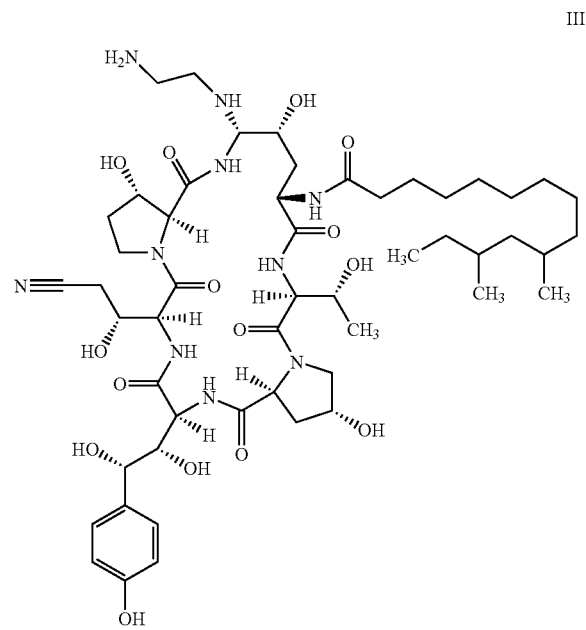

III in a suitable solvent being preferably a mixture of an organic solvent and water, more preferably a mixture of a $C_1$-$C_4$-alcohol and water, B") reducing the compound of formula III or an acid addition salt thereof by catalytic hydrogenation in the presence of propionic acid, C") purifying the product obtained in step B") by reversed phase HPLC in the presence of propionic acid, and D") lyophilizing the fractions obtained in step C").

The suitable solvent used in step A") is inert to reduction. Such solvents may be identified by a skilled person in routine tests. Suitable solvents are e.g. alcohols such as $C_1$-$C_4$ alcohols, e.g. methanol, ethanol or isopropanole, amides such as N,N-dimethylformamide or N-methylpyrrolidon, optionally in combination with water. A preferred suitable solvent is a mixture of an organic solvent, more preferably a mixture of a $C_1$-$C_4$-alcohol, e.g. of ethanol, methanol or isopropanol, and water. One still more preferred solvent is a mixture of isopropanol and water.

A preferred acid addition salt of a compound of formula III as used in step A") is the monoacetate salt, i.e. a compound of formula IIIa:

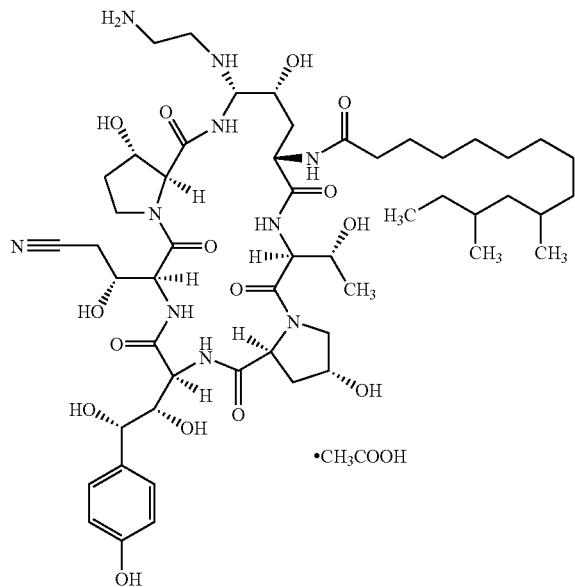

IIIa

The reduction step B") may e.g. be performed as follows: propionic acid is added to the solution or suspension obtained in step A"), and the pH value is adjusted to about 6.5 with a basic agent, e.g. with aqueous ammonia. For the reduction of a compound of formula III or acid addition salts thereof any nitrile reducing agent may be used. Preferably, catalytic hydrogenation is applied. The reduction of a compound of formula III or of an acid addition salt thereof may be performed by applying the catalysts and conditions as described in International Application WO 2007/057141 A1. The compound of formula III corresponds to the compound of formula VI in WO 2007/057141 A1 which is incorporated herein by reference.

Step C"), i.e. purification of the product obtained in step B") by reversed phase HPLC may be performed as follows: after completion of the reduction in step B"), the catalyst may be removed from the reaction mixture, e.g. by filtration, and the remaining filtrate may subsequently be optionally purified by using active charcoal. The filtrate may then be evaporated—optionally after a further filtration—to obtain a viscous residue which may be dissolved in a suitable solvent being a mixture of an organic solvent and water, wherein the organic solvent is preferably a $C_1$-$C_4$-alcohol, e.g. methanol or ethanol or the like, more preferably methanol. Thus, preferably, a mixture of methanol and water is used in step C"). Purification by reversed phase HPLC in the presence of propionic acid may be performed analogous to, e.g. according to step B) as herein described.

Step D"), i.e. lyophilization of the fractions obtained in step C") may be performed analoguous to, e.g. according to step C) as herein described.

The product obtained in step D"), i.e. the lyophilized product is caspofungin propionate according to the invention, particularly in its amorphous form, as e.g. prepared in Example 19 where it is described as caspofungin propionic acid adduct.

In another embodiment, the present invention relates to a process for preparing caspofungin propionate which comprises—in addition to steps A") to D") as described above—the following further steps of:

E") dissolving the lyophilized product obtained in step D") in a mixture of an organic solvent and water, preferably in a mixture of a $C_1$-$C_4$-alcohol and water, F") adding propionic acid and subsequently an acetic acid $C_1$-$C_4$-alkyl ester, preferably ethyl acetate to obtain a suspension, and G") isolating caspofungin propionate from the suspension obtained in step F").

The organic solvent used in step E") is preferably a $C_1$-$C_4$-alcohol, e.g. methanol or ethanol or the like, more preferably ethanol. Thus a preferred solvent being a mixture of an organic solvent and water used in step E") is a mixture of ethanol and water.

The acetic acid $C_1$-$C_4$-alkyl ester used in step F") may be methyl acetate, ethyl acetate, n-propyl acetate or iso-propyl acetate, n-butyl acetate or iso-butyl acetate, preferably ethyl acetate.

Steps E"), F") and G") may be performed analogous to, e.g. according to steps D), E) and F) as herein described.

Preferably, caspofungin propionate obtained in step G") is caspofungin dipropionate, more preferably of formula II, in its crystalline form, as e.g. prepared in Example 19.

Crystalline caspofungin as obtained by one of the herein described processes may be dissolved in water; the obtained solution may subsequently be lyophilized according to known methods to yield caspofungin propionate according to the invention in its amorphous form. In one preferred aspect, the crystalline caspofungin propionate or crystalline caspofungin dipropionate used for the conversion, is treated with humid nitrogen or is exposed to humidity as herein described to remove residual organic solvents before being converted as described above. In another preferred aspect, the obtained amorphous caspofungin propionate shows a defined molar ratio of caspofungin of formula I and propionic acid in the range as described above, and is characterized by a reduced content in residual organic solvents as herein described.

Thus, the present invention provides caspofungin propionate, preferably caspofungin dipropionate, in an amorphous or in a crystalline form, being obtainable, and preferably being obtained, by any one of the above described processes.

Caspofungin in the form of a salt, e.g. in the form of a pharmaceutically acceptable salt, e.g. caspofungin acetate or diacteate, and/or caspofungin as base, which are used as starting material in the herein described processes may be prepared analogously to, e.g. according to the methods disclosed in WO 94/21677 and/or WO96/24613 as mentioned above. Alternatively, caspofungin or one of its salts, and/or a compound for formula III, e.g. a compound of formula IIIa as used in further herein described processes may be produced as described in International Application WO 2007/057141 A1 which is incorporated herein by reference. The compound of formula III and the compound of formula IIIa correspond to the compound of formula VI and to the compound of formula VIa, respectively, in WO 2007/057141 A1. In general, any other salt of caspofungin obtainable from any known source may be used in the herein described processes as starting material.

Caspofungin propionate according to the invention, e.g. caspofungin dipropionate, in its crystalline or amorphous form, may be used as a medicament. Furthermore, caspofungin propionate, e.g. caspofungin dipropionate, in particular in crystalline form or in amorphous form preferably having a defined molar ratio of caspofungin of formula I and propionic acid in the range as described above, may be used for the manufacture of a medicament, e.g. in the form of a pharmaceutical composition of the invention, for the prevention and/or treatment of fungal infections, e.g. caused by Candida species, such as C. albicans, C. tropicalis, C. krusei, C. glabrata and C. pseudotropicalis, and by Aspergillus species, such as A. fumigatus, A. flavus and A. niger, in particular in mammals, such as human patients. Furthermore, caspofungin propionate, e.g. caspofungin dipropionate, in particular in crystalline form or in amorphous form preferably having a defined molar ratio of caspofungin of formula I and propionic acid in the range as described above, may further be used for the manufacture of a medicament, e.g. in the form of a pharmaceutical composition of the invention, for the prevention and/or treatment of infections caused by Pneumocystis jiroveci (previously classified as Pneumocystis carinii), such as P. jiroveci pneumonia, in particular in mammals, such as human patients; said patients who are immuno-compromised e.g. who are suffering from AIDS, are especially susceptible to P. jiroveci pneumonia.

Thus, the present invention relates to the use of caspofungin propionate, in its crystalline and/or amorphous form, as a medicament. Furthermore, the present invention relates to the use of caspofungin propionate, in its crystalline and/or amorphous form for the manufacture of a medicament and/or a pharmaceutical composition for the treatment and/or prevention of fungal infections and/or of infections caused by Pneumocystis jiroveci (previously classified as Pneumocystis carinii).

The caspofungin salt according to the invention, i.e. caspofungin propionate, e.g. caspofungin dipropionate, in crystalline form or amorphous form, is a novel form of the active ingredient caspofungin and therefore offers to the skilled person a valuable option of choice for the manufacture of caspofungin formulations. Advantageously, caspofungin propionate, in particular caspofungin dipropionate, allows large scale preparation, shows good stability and purity, and is easy to handle when preparing the corresponding pharmaceutical compositions comprising it on an industrial scale.

Crystalline caspofungin propionate, e.g. crystalline caspofungin dipropionate, is particularly advantageous for use in the manufacture of pharmaceutical compositions due to its stability, crystal structure and its agglomerate forming properties, as well as due to its easy flowability and its free solubility in water. Crystalline caspofungin propionate may be prepared on a large scale, and residual organic solvents may conveniently be removed by simple process to arrive at pharmaceutically acceptable levels according to the ICH guidelines Q3C(R3) as described above. Furthermore, crystalline caspofungin propionate may easily be converted to an amorphous form having a defined stoichiometry of caspofungin of formula I and of propionic acid, and optionally additionally having a reduced content of residual organic solvents by way of simple procedures as herein described.

Amorphous caspofungin propionate, e.g. amorphous caspofungin dipropionate, shows free solubility in water and may be obtained in a highly pure form, i.e. substantially or completely free of residual organic solvents, according to processes described above, so that it may advantageously be used for preparing pharmaceutical preparations. Additionally, amorphous caspofungin propionate, e.g. amorphous caspofungin dipropionate, may also be prepared on a large scale.

Pharmaceutical compositions, preferably for parenteral administration, e.g. in the form of a reconstituted aqueous solution comprising caspofungin propionate according to the invention show high purity, because they contain only small amounts of total impurities and/or subvisible particles. Additionally, the pharmaceutical compositions of the invention provide enhanced stability for caspofungin propionate therein comprised.

The present invention is illustrated by way of the Examples below, but in no way limited to them. All temperatures are given in degree Celsius and are uncorrected.

In Examples 1 to 5 and 14 to 16, Tables 1 to 4 and 7 to 9 show the components of Compositions 1 to 8 being liquid formulations which are to be lyophilized.

For Examples 6 to 11, vials containing 52.5 mg caspofungin base are used for the methods of analysis therein described. After dilution with 10.5 ml ultrapure water, said vials contain 5.0 mg/ml caspofungin base, i.e. compound of formula I. Each vial thus contains 5% overfill.

Example 1

Comparative

Preparation of Composition 1 comprising caspofungin diacetate and an additional amount of acetate buffer according to Example 1 of EP 0 904 098 B1.

TABLE 1

| Ingredients of Composition 1 | |
|---|---|
| Mannitol | 20 mg/ml |
| Sucrose | 30 mg/ml |
| Acetic acid | 1.5 mg/ml |
| Caspofungin diacetate | 46.6 mg/ml |
| Sodium hydroxide | q.s. |
| pH | 6.0 |

The liquid formulation of Composition 1 was prepared by dissolving 5 g of mannitol and 7.5 g of sucrose in about 200 ml of water. Subsequently the pH value was measured, and acetic acid was added to a final concentration of 1.5 mg/ml, and pH was adjusted with 1 N NaOH to pH 3.7. Subsequently, 11.7 g of caspofungin diacetate corresponding to 46.6 mg/ml caspofungin diacetate or to 42 mg/ml caspofungin calculated as base, were added, the pH was adjusted to a pH value of 6.0 using 1 N NaOH. The volume was adjusted with water to 250 ml and the solution was filtered through a Millex™-GV syringe-driven filter unit with a Durapore™-membrane and a diameter of 0.22 μm, and filled into 15 ml glass vials at 1.25 ml each. The vials were partially stoppered with lyophilization stoppers as commercially available from Helvoet Pharma, and lyophilized until a cake was formed at the bottom of the vial. The lyophilized composition was diluted with 10.5 ml of ultrapure water to obtain a final concentration of 5.0 mg/ml of caspofungin prior to performing analytical tests herein described.

Examples 2 and 3

Preparation of Composition 2 and Composition 3 comprising caspofungin and an additional pH modifier, i.e. acetic acid:

TABLE 2

| Ingredients of | Composition 2 | Composition 3 |
|---|---|---|
| Mannitol | 20 mg/ml | 20 mg/ml |
| Sucrose | 30 mg/ml | 30 mg/ml |
| Acetic acid | q.s. | q.s. |
| Caspofungin diacetate | 46.6 mg/ml | 46.6 mg/ml |
| pH | 6.0 | 6.5 |

The liquid formulations of Compositions 2 and 3 were prepared by dissolving mannitol and sucrose according to Example 1 with a batch size of 100 ml. Subsequently, 46.6 mg/ml caspofungin diacetate, corresponding to 42 mg/ml of caspofungin base, were added, pH value was determined to be 6.59 and was adjusted with 1 N acetic acid to pH 6.0 or pH 6.5, respectively. For Composition 2, 0.1315 mg/ml acetic acid (calculated based on the final volume of liquid formulation) was added which corresponds to a final molar concentration of 2.19 mmol/l additional acetic acid or to a molar ratio of additional acetic acid to caspofungin of 0.0569. After adjustment of volume with water, a pH of 6.05 was obtained. For Composition 3, 0.0188 mg/ml acetic acid (calculated based on the final volume of liquid formulation) was added which corresponds to a final molar concentration of 0.31 mmol/l additional acetic acid or to a molar ratio of additional acetic acid to caspofungin of 0.00813. After adjustment of volume with water, a pH of 6.54 was obtained. Adjustment of volume with water, i.e. to a final volume of 100 ml, filtering of the solution, filling into vials and lyophilization of the product were performed analogously to Example 1. Reconstitution and/or dilution of the lyophilized compositions 2 and 3 were performed analogously to Example 1.

Example 4

Preparation of Composition 4 comprising caspofungin and being free of any additional pH modifier:

TABLE 3

| Ingredients of Composition 4 | |
|---|---|
| Mannitol | 20 mg/ml |
| Sucrose | 30 mg/ml |
| Caspofungin diacetate | 46.6 mg/ml |
| pH | 5.96 |

The liquid formulation of Composition 4 was prepared by dissolving mannitol and sucrose according to Examples 2 and 3 with a batch size of 200 ml. Subsequently 42 mg/ml of caspofungin base, i.e. 46.6 mg/ml of caspofungin diacetate were added, and no further adjustments of the pH value were performed. Adjustment of volume with water, i.e. to a final volume of 200 ml, thereby obtaining a pH value of 5.96, filtering of the solution, filling into vials and lyophilization of the vials were performed analogously to Example 1. Reconstitution and/or dilution of the lyophilized composition 4 were performed analogously to Example 1.

Example 5

Preparation of Composition 5 comprising caspofungin, an additional amount of acetate buffer and additionally EDTA:

TABLE 4

| Ingredients of Composition 5 | |
|---|---|
| Mannitol | 20 mg/ml |
| Sucrose | 30 mg/ml |
| Acetic acid | 1.5 mg/ml |
| EDTA sodium dihydrate | 0.8 mg/ml |
| Caspofungin diacetate | 46.6 mg/ml |
| Sodium hydroxide | q.s. |
| pH | 6.0 |

The liquid formulation of Composition 5 with a batch size of 50 ml was prepared by dissolving mannitol and sucrose and adding acetic acid, adjusting the pH by addition of NaOH and adding caspofungin diacetate as described in Example 1. Subsequently, 0.81 mg/ml of EDTA sodium dihydrate (calculated based on the final adjusted volume) were added, and pH was adjusted to pH 6.0 with 1 N NaOH. Adjustment of volume with water, i.e. to a final volume of 50 ml, thereby obtaining a pH value of 5.99, filtering of the solution, filling into vials and lyophilization of the vials were performed analogously to Example 1. Reconstitution and/or dilution of the lyophilized composition 5 were performed analogously to Example 1.

Example 6

Determination of Total Impurities

The lyophilized Compositions 1 to 5 were either analyzed immediately after lyophilization, i.e. at "0 weeks", or after storage at a temperature of 2° C. to 8° C., i.e. at 5° C. on an average, for 2, 4, 8 or 12 weeks. The compositions were reconstituted by adding 10.5 ml of ultrapure water and were subsequently analyzed for the amount of total impurities according to the method of reversed phase HPLC utilizing a UV detector (mobile phase A: add 1.0 ml trifluoroacetic acid to 2000 ml water; Mobile phase B: mix 1600 ml acetonitrile and 400 ml water and add 1.0 ml trifluoroacetic acid; solvent: water/acetonitrile 70/30 (v/v); stationary phase: Silica RP-18, e.g. Symmetry C18, 3.5 µm, 100 Å—available by Waters; gradient elution; flow rate: 1.5 ml/min; temperature: 20° C.; UV-detection at 220 nm). The limit of quantification was defined as <0.1%. The amounts of total impurities measured in such way were indicative of the stability of the various compositions. FIG. 1 shows total impurities measured expressed as relative peak area in % which were determined by calculating the difference between the total sum of all peak areas measured by HPLC (which represent 100%) and the peak area measured for caspofungin. FIG. 1 shows that all formulations tested showed total impurities of not more than 1.7%. Total impurities seemed higher after storage at 25° C. as compared to storage at 5° C. (data not shown).

Surprisingly, Composition 4 which contained no additional pH modifier or acetate buffer seemed to exhibit similar or even higher stability, i.e. Composition 4 contained significantly less total impurities after storage, as compared to conventional compositions such as Composition 1 containing additional acetate buffer, as seen in FIG. 1. Even after storage at 25° C. for 12 weeks, Composition 4 showed less total impurities than conventional compositions such as Composition 1 (data not shown).

This is unexpected because state of the art documents teach that for conventional compositions like Composition 1, e.g. as described in EP 0 904 098 B1, the presence of an additional buffer is essential for obtaining a stable composition. More particularly, EP 0 904 098 B1 mentions that the presence of an additional amount of an acetate buffer is essential to obtain more stable formulations containing less degradation products—as compared to formulations with another buffer, namely a tartrate buffer. It is therefore surprising that the compositions of the present invention, such as Composition 4, show an equally good or even better stability even without any buffer or pH modifier present in the formulation.

Example 7

Determination of Contents of Compound I

Caspofungin Assay

The lyophilized Compositions 1 to 5 were either analyzed immediately after lyophilization, i.e. at "0 weeks", or after storage at a temperature of 2° C. to 8° C., i.e. at 5° C. on an average, for 2, 4, 8 or 12 weeks. The compositions were reconstituted by adding 10.5 ml of ultrapure water and were subsequently analyzed for the assay of caspofungin according to the method of reversed phase HPLC utilizing a UV detector as described in Example 6. FIG. 2 shows contents of caspofungin, i.e. caspofungin assay expressed as relative peak area in % which were determined by calculating the difference between the total sum of all peak areas measured by HPLC (which represent 100%) and deducting the % area of peaks measured for total impurities. The contents of caspofungin measured in such way are indicative of the stability of the various compositions. Thus FIG. 2 shows that Compositions 2 to 4 had very good stability during storage at 2-8° C. which was comparable to conventional compositions such as Composition 1. Composition 4 being substantially free of any additional pH modifier seemed to show highest stability among all formulations tested by showing the highest content in caspofungin being maintained over the test period. No decrease in stability, i.e. no significant decrease in the content of caspofungin, was observed over time. Similar results were observed for storage at 25° C., where Composition 4 showed the highest content of caspofungin throughout the test period, but there was—for all formulations tested—a slight decay of caspofungin of about 0.5% to about 1% over time (data not shown). Also when stored at 25° C. the compositions of the invention showed good stability, particularly the compositions which were substantially free of any additional pH modifier such as Composition 4. As already discussed in Example 6, this finding was surprising as prior art teaches that the presence of an additional buffer is important for obtaining a stable composition.

Example 8

Determination of Residual Water

Water Content KF

The lyophilized Compositions 1 to 5 were either analyzed immediately after lyophilization or after storage at a temperature of 2° C. to 8° C., i.e. at 5° C. on an average, for 2, 4, 8 or 12 weeks, or at 25° C. for 1, 2, 4, 8 or 12 weeks, respectively. Residual water was determined by the coulometric technique of K. Fischer according to USP <921> method Ic and Ph. Eur. 2.5.32. Residual water values for Compositions 1 to 5 ranged from about 0.2% to about 2.3%. Values tend to be higher after storage at 25° C. In general the residual water content of the tested samples was not expected to negatively influence the quality of the compositions.

Example 9

Determination of Nephelometric Turbidity Units

NTU

The lyophilized Compositions 1 to 5 were either analyzed immediately after lyophilization or after storage at a temperature of 2° C. to 8° C., i.e. at 5° C. on an average, for 2, 4, 8 or 12 weeks, or at 25° C. for 1, 2, 4, 8 or 12 weeks, respectively. The compositions were reconstituted by adding 10.5 ml of ultrapure water and were subsequently analyzed for clarity of solution according to the method of Pharm. Eur. $5^{th}$ ed., Chapter 2.2.1. The results are given in Nephelometric Turbidity Units (NTU) according to the method as therein described. NTU reflect the amount of visible particles in the reconstituted solutions. The NTU values of all compositions stored either at 5° C. or at 25° C. were below 3.0 over time which means that the reconstituted solutions of Compositions 1 to 5 were all clear, i.e. these solutions did not contain any particles being visible to the eye.

Example 10

Determination of pH Value of the Reconstituted Lyophilized Solution

The lyophilized Compositions 1 to 5 were either analyzed immediately after lyophilization or after storage at a temperature of 2° C. to 8° C., i.e. at 5° C. on an average, for 2, 4, 8 or 12 weeks, or at 25° C. for 1, 2, 4, 8 or 12 weeks, respectively. The compositions were reconstituted by adding 10.5 ml of ultrapure water and were subsequently analyzed for pH value using a standard laboratory pH-meter calibrated in the pH range of interest; measurement was performed according to the known principles of potentiometry. The pH values of the tested formulations were all between 6.5 to 6.7 during storage at 5° C. with the exception of Composition 3 for which pH value was 6.9 to 7. When stored at 25° C., the pH values of the tested formulations were between 6.2 to about 6.6—again with the exception of Composition 3 whereof the pH value ranged from 6.9 to about 7.2. This means that the pH value of the most of the compositions of the invention were comparable to those of the conventional Composition 1.

Example 11

Determination of Sub-Visible Particles

The lyophilized Compositions 1 to 5 were either analyzed immediately after lyophilization, i.e. at "0 weeks", or after storage at a temperature of 2° C. to 8° C., i.e. at 5° C. on an average, for 2, 4, 8 or 12 weeks. The compositions were reconstituted by adding 10.5 ml of ultrapure water and were subsequently analyzed for sub-visible particles wherein the number of particles was determined according to USP 27, <788> Particulate matter in injections: Light Obscuration Particle Count test. For Compositions 1 to 4, 3 vials corresponding to a total volume of 31.5 ml were pooled for one determination. For Composition 5, 10 vials were pooled according to the method of USP 27, <788> Particulate matter: Light Obscuration Particle Count Test and Pharm. Eur. $5^{th}$ ed, 2.9.19. Light Obscuration Particle Count Test.

For determination of sub-visible particles it did not seem to be critical whether 3 or 10 vials were pooled for a single measurement. FIGS. 3 and 4 show the results as numbers of sub-visible particles having a size of >10 µm and of >25 µm, respectively, per vial as measured in Compositions 1 to 5. FIGS. 3 and 4 clearly demonstrate that Composition 4 being substantially free of any additional pH modifier surprisingly showed a significantly lower number of sub-visible particles having a size of >10 µm or of >25 µm per vial when compared to all other compositions, including the conventional Composition 1 during storage—with the exception of the value measured after 4 weeks which most probably was an outlier due to a measuring artifact. Also when stored at 25° C. for 12 weeks, Composition 4 showed significantly less sub-visible particles having a size of >10 µm or of >25 µm per vial when compared to conventional Composition 1 (data not shown). Even more surprisingly, Composition 4 also showed significantly less sub-visible particles as compared to Composition 5 which comprises the known particulate formation inhibitor EDTA.

The results for Compositions 2 and 3 being compositions of the invention comprising an additional amount of a pH modifier showed variations between each other and also during storage as is seen form FIGS. 3 and 4. FIG. 4 shows that Compositions 2 and 3 had less sub-visible particles having a size >25 µm per vial when compared to the conventional Composition 1. Numbers of sub-visible particles having a size >10 µm per vial seemed to be mostly comparable to those observed for Composition 1. When stored at 25° C. for 12 weeks, Compositions 2 and 3 showed less sub-visible particles having a size of >10 µm or of >25 µm per vial when compared to conventional Composition 1 (data not shown).

Example 12

Determination of Degradation Product CAF-42

The lyophilized Compositions 1 to 4 were either analyzed immediately after lyophilization, i.e. at "0 weeks", or after storage at a temperature of 2° C. to 8° C., i.e. at 5° C. on an average, or at 25° C., for 12 weeks. The compositions were reconstituted by adding 10.5 ml of ultrapure water and were subsequently analyzed for the presence of CAF-42—being the main degradation product of caspofungin which forms when ethylene diamine is split off the caspofungin molecule—according to the method of reversed phase HPLC as described in Example 6. CAF-42 was determined by HPLC by integration of peak at RRT (relative retention time) of 1.98 applying the chromatographic parameters as described in Example 6. The limit of quantification was defined as <0.1%. CAF-42 is expressed as relative peak area in % which is determined by calculating the ratio of peak area at RRT 1.98 and the sum of peak area for all peaks with a peak area ≧0.1%. Table 5 below shows the amounts of degradation product CAF-42 as determined during storage.

TABLE 5

|  | Composition | | | |
| --- | --- | --- | --- | --- |
|  | 1 | 2 | 3 | 4 |
| Weeks of storage at 2-8° C. | | | | |
| 0 | 0.74 | 0.69 | 0.70 | 0.27 |
| 12 | 0.63 | 0.57 | 0.61 | 0.11 |
| Weeks of storage at 25° C. | | | | |
| 0 | 0.74 | 0.69 | 0.70 | 0.27 |
| 12 | 0.88 | 0.91 | 1.06 | 0.64 |

Values are % relative peak area

Table 5 demonstrates that in particular Composition 4 showed significantly less formation of CAF-42—the main degradation product of caspofungin—than conventional caspofungin compositions such as Composition 1—both when stored at 2-8° C. and at 25° C. for 12 weeks. Storage at 25° C. for 12 weeks is recognized by the US regulatory authorities as stress conditions suitable to test the pharmaceutical stability of pharmaceutical products which are filed to obtain marketing approval by such authority. Therefore, Composition 4 being free of any additional pH modifier, such as e.g. acetic acid, showed better stability in terms of less formation of the degradation product CAF-42 as compared to conventional compositions such as Composition 1, e.g. as described in EP 0 904 098 B1—which better stability was also maintained during storage. As already discussed in Example 6, this finding is surprising in view of EP 0 904 098 B1 which teaches that the presence of an additional acetate buffer is essential for obtaining a more stable formulation of caspofungin generating fewer unwanted degradation products.

Example 13

Determination of Impurity CAF-Dimer 1

The lyophilized Compositions 1 to 4 were either analyzed immediately after lyophilization, i.e. at "0 weeks", or after storage at a temperature of 2° C. to 8° C., i.e. at 5° C. on an average, or at 25° C., for 12 weeks. The compositions were reconstituted by adding 10.5 ml of ultrapure water and were subsequently analyzed for the amount of the impurity CAF-Dimer 1—which may form in caspofungin compositions during storage—according to the method of reversed phase HPLC as described in Example 6. CAF-Dimer 1 was determined by RRT (relative retention time) of 2.41 applying chromatographic parameters as described in Example 6. The limit of quantification was defined as <0.1%. CAF-Dimer 1 is expressed as relative peak area in % which is determined by calculating the ratio of peak area at RRT 2.41 and the sum of peak area for all peaks with a peak area ≧0.1%. Table 6 below shows the amounts of impurity CAF-Dimer 1 as determined during storage.

TABLE 6

|  | Composition | | | |
| --- | --- | --- | --- | --- |
|  | 1 | 2 | 3 | 4 |
| Weeks of storage at 2-8° C. | | | | |
| 0 | 0.28 | 0.26 | 0.26 | <0.1 |
| 12 | 0.27 | 0.24 | 0.24 | <0.1 |
| Weeks of storage at 25° C. | | | | |
| 0 | 0.28 | 0.26 | 0.26 | <0.1 |
| 12 | 0.31 | 0.35 | 0.3 | 0.13 |

Values are % relative peak area

Table 6 demonstrates that in particular Composition 4 showed significantly less formation of the impurity CAF-Dimer 2 when compared to conventional caspofungin compositions such as Composition 1—both when stored at 2-8° C. and at 25° C. for 12 weeks. Thus, Composition 4 being free of any additional pH modifier, such as acetic acid, showed higher purity in terms of less formation of the impurity CAF-Dimer 1—as compared to conventional caspofungin formulations comprising an additional acetate buffer such as Composition 1—which higher purity was also maintained during storage.

Example 14

Preparation of Composition 6 comprising caspofungin and being free of any additional pH modifier:

TABLE 7

| Ingredients of Composition 6 | |
|---|---|
| Mannitol | 20 mg/ml |
| Sucrose | 30 mg/ml |
| Caspofungin diacetate | 46.6 mg/ml |
| pH | 5.96 |

The liquid formulation of Composition 6 was prepared by dissolving mannitol and sucrose according to Example 4 with a batch size of 200 ml. Subsequently 42 mg/ml of caspofungin base, i.e. 46.6 mg/ml of caspofungin diacetate were added, and no further adjustments of the pH value were performed. Adjustment of volume with water, i.e. to a final volume of 200 ml, thereby obtaining a pH value of 5.96, filtering of the solution, filling into vials and lyophilization of the vials were performed analogously to Example 1. In contrast to Example 1, 1.75 ml of solution were filled into vials. Reconstitution and/or dilution of the lyophilized composition 6 were performed analogously to Example 1, by adding 10.5 ml of ultrapure water to obtain a final concentration of 7.0 mg/ml of caspofungin.

Example 15

Preparation of Composition 7 comprising caspofungin and an additional pH modifier, i.e. acetic acid:

TABLE 8

| Ingredients of | Composition 7 |
|---|---|
| Mannitol | 20 mg/ml |
| Sucrose | 30 mg/ml |
| Acetic acid | q.s. |
| Caspofungin diacetate | 46.6 mg/ml |
| pH | 5.0 |

The liquid formulation of Composition 7 was prepared by dissolving mannitol and sucrose according to Example 1 with a batch size of 40 ml. Subsequently, 46.6 mg/ml caspofungin diacetate, corresponding to 42 mg/ml of caspofungin base, were added, pH value was determined to be 5.68 and was adjusted with 1.25 N acetic acid to pH 5.0, respectively. For Composition 7, 0.82 mg/ml acetic acid (calculated based on the final volume of liquid formulation) was added which corresponds to a final molar concentration of 13.75 mmol/l additional acetic acid or to a molar ratio of additional acetic acid to caspofungin of 0.179. After adjustment of volume with water, i.e. to a final volume of 40 ml, a pH of 5.00 was obtained. Filtering of the solution, filling into vials and lyophilization of the product were performed analogously to Example 1. Reconstitution and/or dilution of the lyophilized composition 7 were performed analogously to Example 1.

The following analytical results were obtained by methods according to those described in Examples 8, 9, 10, 11 and 12, respectively, wherein residual water was determined directly after lyophilization and NTU, pH, subvisible particles and CAF-42 were determined directly after reconstitution of the lyophilized product:

Residual water (KF): 0.6%
NTU: 0.1
pH: 5.6
Subvisible particles >10 µm: 143 per vial
Subvisible particles >25 µm: 12 per vial CAF-42 was found to be 0.15%; no further degradation products ≧0.1% were detected.

Example 16

Preparation of Composition 8 comprising caspofungin and an additional pH modifier, i.e. acetic acid/sodium hydroxide:

TABLE 9

| Ingredients of | Composition 8 |
|---|---|
| Mannitol | 20 mg/ml |
| Sucrose | 30 mg/ml |
| Sodium hydroxide/acetic acid | q.s. |
| Caspofungin diacetate | 46.6 mg/ml |
| pH | 7.0 |

The liquid formulations of Composition 8 was prepared by dissolving mannitol and sucrose according to Example 1 with a batch size of 40 ml. Subsequently, 46.6 mg/ml caspofungin diacetate, corresponding to 42 mg/ml of caspofungin base, were added, pH value was determined to be 5.68 and was adjusted with sodium hydroxide/acetic acid to pH 7.0, respectively. After adjustment of volume with water, i.e. to a final volume of 40 ml, a pH of 6.84 was obtained. Filtering of the solution, filling into vials and lyophilization of the product were performed analogously to Example 1. Reconstitution and/or dilution of the lyophilized compositions 8 were performed analogously to Example 1.

The following analytical results were obtained by methods according to those described in Examples 8, 9, 10, 11 and 12, respectively, wherein residual water is determined directly after lyophilization and NTU, pH, subvisible particles and CAF-42 were determined directly after reconstitution of the lyophilized product:

Residual water (KF): 0.67%
NTU: 0.2
pH: 6.7
Subvisible particles >10 µm: 338 per vial
Subvisible particles >25 µm: 19 per vial CAF-42 was found to be 0.26%; no further degradation products ≧0.1% were detected.

Example 17

Preparation of Caspofungin Dipropionate Via Preparative HPLC

Caspofungin diacetate (3.5 g) was dissolved in methanol (50 ml) and water (250 ml) and purified by preparative HPLC using a reversed phase C-8 column and C-8 absorbent as commercially available from YMC Europe GmbH. The product was eluted with a 22 acetonitrile/78 water (v/v) mixture comprising about 0.25% of propionic acid wherein % are weight percentages. The rich cut fractions were pooled and lyophilized to give caspofungin propionic acid adduct (3.7 g) as an amorphous white solid.

The lyophilisate (3.7 g) was dissolved in ethanol (33.3 ml) and water (3.7 ml) at 25° C. Undissolved material was removed by filtration. Propionic acid (224 µl) was added to the filtrate. Subsequently ethyl acetate (44.4 ml) was added within 30 minutes, and the mixture was stirred at 25° C. until crystallization occurred, and was subsequently stirred for about 1 additional hour. Another portion of ethyl acetate (29.6 ml) was added during 4 hours and the crystal suspension was aged for 1 hour. The crystalline solid was filtered off and washed with a mixture of ethanol/water/ethyl acetate (18 ml/2.2 ml/40 ml). The wet cake was dried in vacuo at ambient temperature to yield 2.5 g of crystalline caspofungin dipropionate.

Assay caspofungin: 82.6% (HPLC, calculated as free base)
Water content: 5.5% (according to method by Karl Fischer, coulometer oven/110° C.)
Propionic acid: 10.5% (HPLC)

The XRPD pattern of the product obtained is depicted in FIG. 5. The $^1$H-NMR data and $^{13}$C-NMR data are shown in Table 10.

Methods:
HPLC for assay of caspofungin was performed according to known methods by applying the following conditions: column: YMC-Pack ODS-AQ, S-3 µm, 12 nm, 150×4.6 mm, flow rate: 1.6 ml, column temperature: 25° C., wave length: 210 nm,
Eluent A: 40 mM sulfamic acid
Eluent B. 40 mM sulfamic acid in water/acetonitril/methanol=250/550/30 (w/w/w)
Gradient:

| | Time [min] | | |
|---|---|---|---|
| | 0 | 13 | 35 |
| % B | 40 | 46 | 96 |

HPLC for determination of propionic acid: column: Aquasil C 18, 5 µm, 100 Å (Angstrom unit), 250×4.6 mm, flow rate: 1.0 ml/min, column temperature: 40° C., wave length: 220 nm
Eluent A: 10 mM sulfamic acid
Eluent B: acetonitril
Gradient:

| | Time [min] | | | |
|---|---|---|---|---|
| | 0 | 10 | 15 | 18 | 21 |
| % B | 0 | 0 | 70 | 70 | 0 |

Ethanol: 2.46% Gas chromatography, column DB-WAX, 30 m×0.53 mm ID, 1.0 µm layer, flow rate: 2.5 ml He/min, detector: FID 250° C., injector: 200° C., head space sampler.
Temperature Program:

| | Time [min] | | | |
|---|---|---|---|---|
| | 0 | 6 | 21 | 23 |
| Temp. [° C.] | 60 | 60 | 160 | 220 |

X-Ray Powder Diffraction (XRPD) pattern was measured under the following conditions:
Equipment: X-Ray Powder Diffractometer D-8 (AXS-BRUKER), theta-theta-goniometer, sample changer, target: Copper, Kα1+Kα2 wavelength: 0.15406 nm, parallel beam optics (receiving soller-slit: 0.07 mm), energy-dispersive counter, standard sample holders.

Data collection: 40 kV, 40 mA, continuous scan 2-40° theta/2theta, step size: 0.01, counting time 2 seconds; ambient conditions (20° C.±5° C., and 30%-60% humidity).

Example 18

Preparation of Caspofungin Dipropionate Via Caspofungin Base

Caspofungin diacetate (5.0 g) was dissolved in water (400 ml). The pH value of the solution was carefully adjusted to 9.0 by slowly adding 1 N NaOH. The resulting suspension was stirred for 30 minutes and then filtered. The filter cake was thoroughly washed with water. The wet product was dissolved in ethanol (36.0 ml) containing propionic acid (616 µl). The solution was treated with charcoal (0.5 g) and filtered. Ethyl acetate (60 ml) was added to the filtrate within 30 minutes which was subsequently seeded and stirred for 1 hour at 25° C. Another portion of ethyl acetate (40 ml) was added during 4 hours and the crystal suspension was aged for 1 hour. The solid was filtered off and dried in vacuo at ambient temperature to yield 3.4 g of crystalline caspofungin dipropionate.

Example 19

Preparation of Caspofungin Dipropionate Via Preparative HPLC

A compound of formula IIIa as herein described is prepared according to Example 7 and Example 9 of International Application WO 2007/057141 A1 which are incorporated herein by reference. The compound of formula IIIa corresponds to the compound of formula VIa in WO 2007/057141 A1. 1 g of compound of formula IIIa is dissolved in a mixture of 2-propanol (24 ml) and water (4 ml). Propionic acid (4.4 ml) and 25% aqueous ammonia (2.2 g) are added giving a solution with a pH value of approximately 6.5. After the addition of 5% Rh/Al$_2$O$_3$ (100 mg) the mixture is vigorously stirred at 30° C. under an hydrogen atmosphere at ambient pressure until less than 0.5% of starting material remains. The catalyst is filtered off and the filtrate is stirred with activated charcoal (100 mg). The suspension is filtered and the filtrate is evaporated. The residue is dissolved in methanol (12.5 ml) and water (62.5 ml) and purified by preparative HPLC using a reversed phase C-8 column as available from YMC Europe GmbH. The product is eluted with a 22 acetonitrile/78 water (v/v) mixture comprising about 0.25% of propionic acid wherein % are weight percentages. The rich cut fractions are pooled and lyophilized to give caspofungin propionic acid adduct (0.8 g) as an amorphous white solid.

The lyophilisate is crystallized, isolated and dried as described in Example 17 to yield 0.55 g crystalline caspofungin dipropionate.

Example 20

Preparation of a Pharmaceutical Composition Comprising Caspofungin Dipropionate

| Ingredients of liquid composition | |
|---|---|
| Caspofungin dipropionate | 47.7 mg/ml |
| corresponding to Caspofungin | 42 mg/ml |
| Mannitol | 20 mg/ml |
| Sucrose | 30 mg/ml |
| Propionic acid | 1.85 mg/ml |
| Sodium hydroxide | q.s. ad pH 6.0 |
| Water for Injection | ad 1.00 ml |

The liquid composition was prepared by dissolving mannitol and sucrose in water to obtain a solution with a concentration of 40 mg/ml and 60 mg/ml, respectively, adding 5 ml of the obtained mixture into a beaker glass, adding 120 µl of 154.2 mg/ml propionic acid to obtain a pH of 3.21 and adjusting the pH to 3.64 by addition of 10 µl 1 N NaOH. 533.3 mg of crystalline caspofungin dipropionate (as is assay of 78.6%) prepared as described in Example 17 were added to result in a final concentration corresponding to 42 mg/ml caspofungin calculated as base. After dissolution of caspofungin dipropionate a pH of 5.08 was obtained which was adjusted to 6.0 by addition of 60 µl 1 N NaOH. The solution was transferred into a 10 ml volumetric flask and filled up with water to a final volume of 10 ml; the final solution had a density of 1.02396 g/ml at ambient temperature measured by gravimetric weighing of volumetric flask. 476 µl of the solution were transferred into 6 R glass vials as commercially available from ISO GmbH, Bad Königshofen, Germany, with an Eppendorf Multipette™. Vials were partially stoppered and lyophilized until a cake was formed at the bottom of the vial wherein freeze-drying was performed using a freeze drier as commercially available as Christ Epsilon 2-6 D™ freeze-drier. Briefly, freeze-drying was performed as follows: the glass vials were stored for 60 minutes at 5° C. Temperature was lowered from +5° C. to −45° C. within 50 minutes. Temperature was kept at −45° C. for 150 minutes and primary drying was started by applying a vacuum of 0.04 mbar. Temperature was raised to −40° C. within 5 minutes. Primary drying was performed by holding the temperature at −40° C. and the vacuum at 0.04 mbar for 960 minutes. For secondary drying, the vacuum was reduced to 0.011 mbar. Temperature was raised to +15° C. with a ramp speed of 1 K/min. Secondary drying was performed at +15° C. within 3 hours at a vacuum of 0.011 mbar.

Each lyophilized vial contained 22.7 mg caspofungin dipropionate corresponding to 20 mg of caspofungin base, 9.5 mg mannitol, 14.3 mg sucrose and 0.88 mg propionic acid. Reconstitution was performed by addition of 4.0 ml ultrapure water resulting in a reconstituted solution having final concentration of 5.0 mg/ml caspofungin and showing high purity, i.e. an amount of total impurities of about 1.30% (as determined by HPLC as described below). Ultrapure water is water which is obtained from a ultrapure water purification system, e.g. a Millipore Gradient A10 with UV-lamp and ultrafiltration. Ultrapure water has properties which are comparable to water for injection USP and Ph. Eur. The pH of the reconstituted solution was 6.4. Subvisible particles >10 µm: 390 per vial; subvisible particles >25 µm: 18 per vial (subvisible particles were determined by the method according to USP 29, <788> Particulate matter in injections: Light Obscuration Particle Count test; 3 vials were reconstituted each with 4 ml of water, the obtained solution was transferred into Falcon™ tubes and filled up with particulate-free water to about 30 ml).

HPLC for Determination of Total Impurities:

According to the method of reversed phase HPLC utilizing a UV detector (mobile phase A: 0.61 g sulfamic acid were dissolved in 767.5 g water and 182.8 g acetonitrile; mobile phase B: 0.15 g sulfamic acid were dissolved in 250 g water and 589.5 g acetonitrile); solvent: sulfamic acid/water/acetonitrile 0.61 g/930 ml/70 ml; column, 150×4.6 mm ID; stationary phase: Silica RP-18, e.g. Symmetry C18, 3.5 µm, 100 Å (Angstrom unit)—as commercially available by Waters Corporation, Massachusetts, USA; gradient elution; flow rate: 1.5 ml/min; temperature: 25° C.; UV-detection at 210 nm. The limit of quantification was defined as <0.1%. All peaks in the test solution referring to related substances of caspofungin were evaluated using a caspofungin reference solution.

Example 21

Preparation of a Pharmaceutical Composition Comprising Caspofungin Dipropionate

| Ingredients of liquid composition | |
|---|---|
| Caspofungin dipropionate | 47.7 mg/ml |
| corresponding to Caspofungin | 42 mg/ml |
| Mannitol | 20 mg/ml |
| Sucrose | 30 mg/ml |
| Propionic acid | 0.2315 mg/ml |
| Water for Injection | ad 1.00 ml |

The liquid composition was prepared by dissolving mannitol and sucrose in water to obtain a solution with a concentration of 40 mg/ml and 60 mg/ml, respectively, adding 5 ml of the obtained mixture into a beaker glass and adding 533.5 mg of crystalline caspofungin dipropionate (as is assay of 78.6%) prepared as described in Example 17 to result in a final concentration corresponding to 42 mg/ml caspofungin calculated as base. Caspofungin dipropionate dissolved within about 3 minutes, a pH value of 6.99 was obtained. The pH value was adjusted to 6.0 by addition of 25 µl of 1.25 N propionic acid solution. The obtained solution was filled up with water to a final volume of 10 ml. 476 µl of this solution were transferred into 10 R glass vials as commercially available from ISO GmbH, Bad Königshofen, Germany, with a Eppendorf Multipette™. Vials were partially stoppered and lyophilized until a cake was formed at the bottom of the vial wherein freeze-drying was performed using a freeze drier as commercially available as Christ Epsilon 2-6 D™ freeze-drier and applying the procedure described in Example 20. Each lyophilized vial contained 22.7 mg caspofungin dipropionate corresponding to 20 mg of caspofungin base, 9.5 mg mannitol, 14.3 mg sucrose and 0.1102 mg propionic acid. Reconstitution was performed by addition of 4.0 ml ultrapure water resulting in a reconstituted solution having final concentration of 5.0 mg/ml caspofungin and showing high purity, i.e. an amount of total impurities of about 0.65% (HPLC as described in Example 20). The pH of the reconstituted solution was 6.2. Subvisible particles >10 µm: 226 per vial; subvisible particles >25 µm: 5 per vial (subvisible particles were determined by the method according to USP 29, <788> Particulate matter in injections: Light Obscuration Particle Count test, as described in Example 20).

The XRPD pattern of the lyophilized product is depicted in FIG. 6; XRPD pattern was measured as described in Example 17.

Example 22

Preparation of a Pharmaceutical Composition Comprising Caspofungin Dipropionate

| Ingredients of liquid composition | |
|---|---|
| Caspofungin dipropionate | 47.7 mg/ml |
| corresponding to Caspofungin | 42 mg/ml |
| Mannitol | 20 mg/ml |
| Sucrose | 30 mg/ml |
| Water for Injection | ad 1.00 ml |

The liquid composition was prepared by dissolving mannitol and sucrose in water to obtain a solution with a concentration of 40 mg/ml and 60 mg/ml, respectively, adding 5 ml of the obtained mixture into a beaker glass, and adding 533.5 mg of crystalline caspofungin dipropionate (as is assay of 78.6%) prepared as described in Example 17 to result in a final concentration corresponding to 42 mg/ml caspofungin calculated as base. Caspofungin dipropionate dissolved within about 3 minutes; a pH value of 6.99 was obtained. The resulting solution was filled up with water to a final volume of 10 ml. 476 μl of this solution were transferred into 10 R glass vials with a Eppendorf Multipette™. Vials were partially stoppered and lyophilized until a cake was formed at the bottom of the vial wherein freeze-drying was performed using a freeze drier as commercially available as Christ Epsilon 2-6 D™ freeze-drier and applying the procedure described in Example 20. Each lyophilized vial contained 22.7 mg caspofungin dipropionate corresponding to 20 mg of caspofungin base, 9.5 mg mannitol and 14.3 mg sucrose. Reconstitution was performed by addition of 4.0 ml ultrapure water resulting in a reconstituted solution having final concentration of 5.0 mg/ml caspofungin and showing high purity, i.e. an amount of total impurities of about 0.95% (HPLC as described in Example 20). The pH of the reconstituted solution was 6.3. Subvisible particles >10 μm: 315 per vial; subvisible particles >25 μm: 8 per vial (subvisible particles were determined by the method according to USP 29, <788> Particulate matter in injections: Light Obscuration Particle Count test; as described in Example 20).

Example 23

Preparation of a Pharmaceutical Composition Comprising Caspofungin Dipropionate 1.25 ml of a solution which has been prepared and filled up with water to a final volume of 10 ml as described in Example 20 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 59.6 mg caspofungin dipropionate corresponding to 52.5 mg of caspofungin base, 25 mg mannitol and 37.5 mg sucrose and 2.31 mg propionic acid. Reconstitution is performed by addition of 10.5 ml ultrapure water resulting in a reconstituted solution having final concentration of 5.0 mg/ml caspofungin and showing high purity, i.e. an amount of total impurities of about 1.1% (HPLC as described in Example 20). The pH of the reconstituted solution is 6.4. Subvisible particles >10 μm: 512 per vial; subvisible particles >25 μm: 16 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

Example 24

Preparation of a Pharmaceutical Composition Comprising Caspofungin Dipropionate 1.75 ml of a solution which has been prepared and filled up with water to a final volume of 10 ml as described in Example 20 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 83.5 mg caspofungin dipropionate corresponding to 73.5 mg of caspofungin base, 35 mg mannitol and 52.5 mg sucrose and 3.24 mg propionic acid. Reconstitution is performed by addition of 10.5 ml ultrapure water resulting in a reconstituted solution having final concentration of 7.0 mg/ml caspofungin and showing high purity, i.e. an amount of total impurities of about 1.0% (HPLC as described in Example 20). The pH of the reconstituted solution is 6.5. Subvisible particles >10 μm: 485 per vial; subvisible particles >25 μm: 12 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

Example 25

Preparation of a Pharmaceutical Composition Comprising Caspofungin Dipropionate 1.25 ml of a solution which has been prepared and filled up with water to a final volume of 10 ml as described in Example 21 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 59.6 mg caspofungin dipropionate corresponding to 52.5 mg of caspofungin base, 25 mg mannitol and 37.5 mg sucrose and 0.29 mg propionic acid. Reconstitution is performed by addition of 10.5 ml ultrapure water resulting in a reconstituted solution having final concentration of 5.0 mg/ml caspofungin and showing high purity, i.e. an amount of total impurities of about 1.1% (HPLC as described in Example 20). The pH of the reconstituted solution is 6.4. Subvisible particles >10 μm: 512 per vial; subvisible particles >25 μm: 16 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

Example 26

Preparation of a Pharmaceutical Composition Comprising Caspofungin Dipropionate 1.75 ml of a solution which has been prepared and filled up with water to a final volume of 10 ml as described in Example 21 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 83.5 mg caspofungin dipropionate corresponding to 73.5 mg of caspofungin base, 35 mg mannitol and 52.5 mg sucrose and 0.40 mg propionic acid. Reconstitution is performed by addition of 10.5 ml ultrapure water resulting in a reconstituted solution having final concentration of 7.0 mg/ml caspofungin and showing high purity, i.e. an amount of total impurities of about 1.2% (HPLC as described in Example 20). The pH of the reconstituted solution is 6.4. Subvisible particles >10 μm: 615 per vial; subvisible particles >25 μm: 21 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

Example 27

Preparation of a Pharmaceutical Composition Comprising Caspofungin Dipropionate 1.25 ml of a solution which has been prepared and filled up with water to a final volume of 10 ml as described in Example 22 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 59.6 mg caspofungin dipropionate corresponding to 52.5 mg of caspofungin base, 25 mg mannitol and 37.5 mg sucrose. Reconstitution is performed by addition of 10.5 ml ultrapure water resulting in a reconstituted solution having final concentration of 5.0 mg/ml caspofungin and showing high purity, i.e. an amount of total impurities of about 1.3% (HPLC as described in Example 20). The pH of the reconstituted solution is 6.5. Subvisible particles >10 μm: 395 per vial; subvisible particles >25 μm: 13 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

Example 28

Preparation of a Pharmaceutical Composition Comprising Caspofungin Dipropionate 1.75 ml of a solution which has been prepared and filled up with water to a final volume of 10 ml as described in Example 22 are transferred into 10 R glass vials with an Eppendorf Multipette™. Vials are partially stoppered and lyophilized until a cake is formed at the bottom of the vial wherein freeze-drying is performed using a freeze drier as commercially available as Christ Epsilon 2-6 D™ freeze-drier and applying the procedure described in Example 20. Process time is adjusted to ensure finishing of primary and secondary drying steps, i.e. process step is prolonged until product temperature reaches temperature of shelf. Each lyophilized vial contains 83.5 mg caspofungin dipropionate corresponding to 73.5 mg of caspofungin base, 35 mg mannitol and 52.5 mg sucrose. Reconstitution is performed by addition of 10.5 ml ultrapure water resulting in a reconstituted solution having final concentration of 7.0 mg/ml caspofungin and showing high purity, i.e. an amount of total impurities of about 0.9% (HPLC as described in Example 20). The pH of the reconstituted solution is 6.4. Subvisible particles >10 μm: 587 per vial; subvisible particles >25 μm: 23 per vial (subvisible particles are determined by the method according to USP 29, <788> Particulate matter in injections: Light Obscuration Particle Count test; as described in Example 20; 3 vials are reconstituted each with 10.5 ml of water, the obtained solutions are transferred into Falcon™ tubes).

The invention claimed is:
1. A pharmaceutical composition comprising:
a pharmaceutically acceptable salt of caspofungin; and
a pharmaceutically acceptable amount of an excipient effective to form a lyophilized cake, wherein said composition is substantially free of any additional pH modifier.
2. The pharmaceutical composition of claim 1, wherein the pharmaceutically acceptable salt of caspofungin comprises an acid addition salt with an organic acid comprising at least one organic acid selected from the group consisting of acetic, citric, tartaric, propionic, succinic, oxalic, malic, maleic, lactic, glutamic, and pamoic acid.
3. The pharmaceutical composition of claim 1, wherein the pharmaceutically acceptable salt of caspofungin is caspofungin diacetate.
4. The pharmaceutical composition of claim 1, wherein the excipient comprises one or more bulking agents.
5. The pharmaceutical composition of claim 4, wherein the bulking agents comprise mannitol, sucrose or a combination thereof.
6. The pharmaceutical composition of claim 1, comprising a) about 0.1 mg/ml to about 500 mg/ml caspofungin calculated as caspofungin base, and b) about 10 mg/ml to about 200 mg/ml of the excipient, the excipient comprising at least one bulking agent, and water.
7. The pharmaceutical composition of claim 1, comprising a) about 42 mg/ml caspofungin calculated as caspofungin base, and b) about 50 mg/ml of the excipient comprising a mixture of about 20 mg/ml of mannitol and about 30 mg/ml of sucrose, and water.

8. The pharmaceutical composition of claim 1, wherein the composition has a pH value of about 5 to about 7.

9. A lyophilized powder formed from the pharmaceutical composition according to one of claims 2, 3, and 4-8 being suitable for reconstitution to form a liquid composition for parenteral administration,
wherein the lyophilized powder is substantially free of any additional pH modifier.

10. A reconstituted pharmaceutical composition formed from the lyophilized powder according to claim 9 wherein the reconstituted pharmaceutical composition is substantially free of any additional pH modifier.

11. The reconstituted pharmaceutical composition of claim 10, wherein the composition has a pH value of about 5 to about 8.

12. A pharmaceutical composition of claim 1, which is a stable formulation.

13. The reconstituted pharmaceutical composition of claim 10, having less than 500 sub-visible particles per vial, the particles having a size greater than 10 μm.

14. A method of using a pharmaceutical composition for the manufacture of a medicament for the prevention and/or treatment of fungal infections or conditions caused by *Candida* sp, and/or by *Aspergillus* sp, and/or by *Pneumocystis jiroveci* in a mammal, wherein the pharmaceutical composition comprises:
a pharmaceutically acceptable salt of caspofungin; and
a pharmaceutically acceptable amount of an excipient effective to form a lyophilized cake, wherein the composition is substantially free of any additional pH modifier, the method comprising forming the medicament from the pharmaceutical composition.

15. A process for preparing a pharmaceutical composition containing a pharmaceutically acceptable salt of caspofungin, which process comprises the steps of:
1) dissolving a bulking agent or a combination of bulking agents in water to form a solution;
2) adding a pharmaceutically acceptable salt of caspofungin to the solution and dissolving the salt of caspofungin in the solution;
3) filtering the solution obtained in step 2) to obtain a filtered solution;
4) freezing the filtered solution obtained in step 3) to form a frozen solution; and
5) freeze drying the frozen solution to form the pharmaceutical composition, wherein the composition is substantially free of any additional pH modifier.

16. The pharmaceutical composition of claim 1, comprising
a) about 20 mg/ml to about 60 mg/ml caspofungin calculated as caspofungin base, and
b) about 40 mg/ml to about 60 mg/ml of the excipient, the excipient comprising at least one bulking agent, and water.

17. The pharmaceutical composition of claim 1, wherein the composition has a pH value of about 5.5 to about 6.5.

18. The pharmaceutical composition of claim 1, wherein the composition has a pH value of about 6.0.

19. The reconstituted pharmaceutical composition of claim 10, wherein the aqueous solution comprises distilled or sterile water for injection.

20. The reconstituted pharmaceutical composition of claim 10, wherein the aqueous solution comprises bacteriostatic water for injection which optionally comprises methylparaben and/or propylparaben and/or 0.9% benzyl alcohol.

21. The reconstituted pharmaceutical composition of claim 10, wherein the aqueous solution comprises saline or physiological saline.

22. The reconstituted pharmaceutical composition of claim 21, wherein the saline comprises at least one of a 0.9% solution of sodium chloride, a 0.45% or a 0.225% solution of sodium chloride.

23. The reconstituted pharmaceutical composition of claim 10, wherein the composition has a pH value of about 6.0 to about 7.5.

24. The reconstituted pharmaceutical composition of claim 10, wherein the reconstituted pharmaceutical composition is injectable intravenously.

25. A method of treating a patient for a fungal infection comprising:
reconstituting a pharmaceutical composition by combining a lyophilized powder according to claim 9 with an aqueous solution to form the reconstituted pharmaceutical composition that is free of visual particles; and
injecting the reconstituted pharmaceutical composition intravenously into a patient.

* * * * *

UNITED STATES PATENT AND TRADEMARK OFFICE
CERTIFICATE OF CORRECTION

PATENT NO. : 8,232,245 B2  
APPLICATION NO. : 12/374489  
DATED : July 31, 2012  
INVENTOR(S) : Christian Welz et al.

Page 1 of 2

It is certified that error appears in the above-identified patent and that said Letters Patent is hereby corrected as shown below:

In the specification:

Column 4, lines 59 and 64, replace "C." with --C--.

Column 5, lines 5 and 14, replace "C." with --C--.

Column 10, lines 31, 33, and 63, replace "C." with --C--.

Column 11, lines 1 and 3, replace "C." with --C--.

Column 13, line 15, replace "C." with --C--.

Column 16, line 64, replace "9.01" with --9.0--.

Column 18, lines 51, 52, and 65-67, replace "C." with --C--.

Column 23, lines 40 and 41, replace "C." with --C--.

Column 31, lines 20 and 32, replace "C." with --C--.

Column 32, line 7, replace "C." with --C--.

Column 38, lines 32, 42, 52, 53, and 60, replace "C." with --C--.

Column 39, lines 18, 31, 39, 43, 59, and 60, replace "C." with --C--.

Column 40, lines 9, 10, 18, 30, 31, 38, 39, and 52, replace "C." with --C--.

Column 41, lines 9, 26, 37, and 38, replace "C." with --C--.

Column 42, lines 5, 6, 30, 31, and 64, replace "C." with --C--.

Column 44, line 67, replace "C." with --C--.

Signed and Sealed this  
Second Day of July, 2013

Teresa Stanek Rea  
*Acting Director of the United States Patent and Trademark Office*

CERTIFICATE OF CORRECTION (continued)
U.S. Pat. No. 8,232,245 B2

In the specification:

Column 45, lines 21, 38, 53, and 61, replace "C." with --C--.

Column 46, lines 6 and 52, replace "C." with --C--.

Column 47, lines 42, 43, 45, 46, 48, and 50, replace "C." with --C--.

Column 48, line 14, replace "C." with --C--.

In the claims:

Column 53, line 13, in Claim 10, after "9" insert --reconstituted with an aqueous solution,--.